US010251408B2

(12) United States Patent
Tachibana

(10) Patent No.: US 10,251,408 B2
(45) Date of Patent: Apr. 9, 2019

(54) CATECHIN FUNCTION ENHANCEMENT METHOD

(71) Applicant: KYUSHU UNIVERSITY, NATIONAL UNIVERSITY CORPORATION, Fukuoka-shi, Fukuoka (JP)

(72) Inventor: Hirofumi Tachibana, Fukuoka (JP)

(73) Assignee: Kyushu University, National University Corporation, Fukuoka-shi, Fukuoka (JP)

( * ) Notice: Subject to any disclaimer, the term of this patent is extended or adjusted under 35 U.S.C. 154(b) by 0 days.

(21) Appl. No.: 15/321,134

(22) PCT Filed: Jun. 25, 2015

(86) PCT No.: PCT/JP2015/068302
§ 371 (c)(1),
(2) Date: Dec. 21, 2016

(87) PCT Pub. No.: WO2015/199169
PCT Pub. Date: Dec. 30, 2015

(65) Prior Publication Data
US 2017/0156361 A1 Jun. 8, 2017

(30) Foreign Application Priority Data
Jun. 27, 2014 (JP) ................................. 2014-132891

(51) Int. Cl.
| A61K 36/00 | (2006.01) |
| A23F 3/16 | (2006.01) |
| A61K 31/353 | (2006.01) |
| A61K 31/7048 | (2006.01) |
| A23L 33/105 | (2016.01) |
| A61K 31/352 | (2006.01) |
| A61K 36/752 | (2006.01) |
| A61K 36/82 | (2006.01) |

(52) U.S. Cl.
CPC .............. *A23F 3/16* (2013.01); *A23L 33/105* (2016.08); *A61K 31/352* (2013.01); *A61K 31/353* (2013.01); *A61K 31/7048* (2013.01); *A61K 36/752* (2013.01); *A61K 36/82* (2013.01); *A23V 2002/00* (2013.01)

(58) Field of Classification Search
CPC ..................................................... A61K 36/00
See application file for complete search history.

(56) References Cited

U.S. PATENT DOCUMENTS

| 6,379,714 B1 | 4/2002 | Khwaja et al. | |
| 2011/0274680 A1* | 11/2011 | Mazed .................. | A61K 36/02 424/94.4 |

FOREIGN PATENT DOCUMENTS

| JP | 2000-512621 A | 9/2000 |
| JP | 2003-507486 A | 2/2003 |
| JP | 2004-75619 A | 3/2004 |
| JP | 2005-75805 A | 3/2005 |
| JP | 2009-55905 A | 3/2009 |
| WO | WO 01/1439 A1 | 3/2001 |

OTHER PUBLICATIONS

Zhang et al, Effect of Eriodictyol on Glucose Uptake and Insulin Resistance in Vitro. Journal of agricultural and food chemistry (2012), vol. 60, No. 31, p. 7652-7658 (Year: 2012).*
Basolo et al., "Expression of the $M_r$ 67,000 laminin receptor is an adverse prognostic indicator in human thyroid cancer: an immunohistochemical study," Clinical Cancer Research, vol. 2, Oct. 1996, pp. 1777-1780 (5 pages total).
Britschgi et al., "Epigallocatechin-3-gallate induces cell death in acute myeloid leukaemia cells and supports all-trans retinoic acid-induced neutrophil differentiation via death-associated protein kinase 2," British Journal of Haematology, vol. 149, 2010 (published online Jan. 20, 2010), pp. 55-64.
Byun et al., "TLR4 signaling inhibitory pathway induced by green tea polyphenol epigallocatechin-3-gallate through 67-kDa laminin receptor," The Journal of Immunology, vol. 185, 2010, pp. 33-45.
Chen et al., "Down-regulation of 67LR reduces the migratory activity of human glioma cells in vitro," Brain Research Bulletin, vol. 79, 2009 (available online May 13, 2009), pp. 402-408.
Cioce et al., "Increased expression of the laminin receptor in human colon cancer," Journal of the National Cancer Institute, vol. 83, No. 1, Jan. 2, 1991, pp. 29-36.
Fontanini et al., "67-Kilodalton laminin receptor expression correlates with worse prognostic indicators in non-small cell lung carcinomas," Clinical Cancer Research, vol. 3, Feb. 1997, pp. 227-231 (6 pages total).
Fujimura et al., "A lipid raft-associated 67 kDa laminin receptor mediates suppressive effect of epigallocatechin-3-O-gallate on FcεRI expression," Biochemical and Biophysical Research Communications, vol. 336, 2005 (available online Aug. 29, 2005), pp. 674-681.
Gundimeda et al., "Green tea catechins potentiate the neuritogenic action of brain-derived neurotrophic factor: role of 67-kDa laminin receptor and hydrogen peroxide," Biochemical and Biophysical Research Communications, vol. 445, 2014 (available online Feb. 4, 2014), pp. 218-224.
Holy et al., "Laminin receptor activation inhibits endothelial tissue factor expression," Journal of Molecular and Cellular Cardiology, vol. 48, No. 6, 2010, pp. 1138-1145 (26 pages total).
International Search Report (Form PCT/ISA/210), dated Sep. 1, 2015, for International Application No. PCT/JP2015/068302.
Kanda et al., "MCP-1 contributes to macrophage infiltration into adipose tissue, insulin resistance, and hepatic steatosis in obesity," The Journal of Clinical Investigation, vol. 116, No. 6, Jun. 2006, pp. 1494-1505.
Khan et al. "Targeting multiple signaling pathways by green tea polyphenol (−)-epigallocatechin-3-gallate," Cancer Research, vol. 66, No. 5, Mar. 1, 2006, pp. 2500-2505 (7 pages total).
Kumazoe et al., "67-kDa laminin receptor increases cGMP to induce cancer-selective apoptosis," The Journal of Clinical Investigation, vol. 123, No. 2, Feb. 2013, pp. 787-799.

(Continued)

*Primary Examiner* — Qiuwen Mi
(74) *Attorney, Agent, or Firm* — Birch, Stewart, Kolasch & Birch, LLP

(57) ABSTRACT

The present invention provides a composition comprising a tea extract or a catechin and a citrus fruit extract or a flavanone or a glycoside thereof.

7 Claims, 19 Drawing Sheets

(56) References Cited

OTHER PUBLICATIONS

Kumazoe et al., "Phosphodiesterase 5 inhibitor acts as a potent agent sensitizing acute myeloid leukemia cells to 67-kDa laminin receptor-dependent apoptosis," FEBS letters, vol. 587, 2013 (available online Aug. 1, 2013), pp. 3052-3057.

Ménard et al., "The 67 kDa laminin receptor as a prognostic factor in human cancer," Breast Cancer Research and Treatment, vol. 52, 1998, pp. 137-145.

Ménard et al., "New insights into the metastasis-associated 67 kD laminin receptor," Journal of Cellular Biochemistry, vol. 67, 1997, pp. 155-165 (12 pages total).

Nelson et al., "The 67 kDa laminin receptor: structure, function and role in disease," Bioscience Reports, vol. 28, No. 1, 2008, pp. 33-48.

Sanjuán et al., "Overexpression of the 67-kD laminin receptor correlates with tumour progression in human colorectal carcinoma," Journal of Pathology, vol. 179, 1996, pp. 376-380.

Santilli et al., "Polyphenol E enhances the antitumor immune response in neuroblastoma by inactivating myeloid suppressor cells," Clinical Cancer Research, vol. 19, No. 5, Mar. 1, 2013, pp. 1116-1125.

Shammas et al., "Specific killing of multiple myeloma cells by (−)-epigallocatechin-3-gallate extracted from green tea: biologic activity and therapeutic implications," Blood, vol. 108, No. 8, Oct. 15, 2006 (published online Jun. 29, 2006), pp. 2804-2810 (8 pages total).

Shanafelt et al., "Phase I trial of daily oral Polyphenon E in patients with asymptomatic Rai stage 0 to II chronic lymphocytic leukemia," Journal of Clinical Oncology, vol. 27, No. 23, Aug. 10, 2009 (published online May 26, 2009), pp. 3808-3814.

Tachibana et al., "A receptor for green tea polyphenol EGCG," Nature Structural and Molecular Biology, vol. 11, No. 4, Apr. 2004 (published online Mar. 14, 2004), pp. 380-381.

Tsukamoto et al., "Green tea polyphenol EGCG induces lipid-raft clustering and apoptotic cell death by activating protein kinase C$\delta$ and acid sphingomyelinase through a 67 kDa laminin receptor in multiple myeloma cells," Biochemical Journal, vol. 443, 2012 (published Jan. 19, 2012), pp. 525-534.

Umeda et al., "Epigallocatechin-3-O-gallate disrupts stress fibers and the contractile ring by reducing myosin regulatory light chain phosphorylation mediated through the target molecule 67kDa laminin receptor," Biochemical and Biophysical Research Communications, vol. 333, 2005 (available online May 31, 2005), pp. 628-635.

Umeda et al., "Green tea polyphenol epigallocatechin-3-gallate signaling pathway through 67-kDa laminin receptor," Journal of Biological Chemistry, vol. 283, No. 6, Feb. 8, 2008 (published online Dec. 12, 2007), pp. 3050-3058 (10 pages total).

Umeda et al., "Involvement of 67-kDa laminin receptor-mediated myosin phosphatase activation in antiproliferative effect of epigallocatechin-3-O-gallate at a physiological concentration on Caco-2 colon cancer cells," Biochemical and Biophysical Research Communications, vol. 371, 2008 (available online Apr. 25, 2008), pp. 172-176.

Vacca et al., "Melanocyte tumor progression is associated with changes in angiogenesis and expression of the 67-kilodalton laminin receptor," Cancer, vol. 72, No. 2, Jul. 15, 1993, pp. 455-461.

Yan et al., "Multiple functions of immunoglobulin A in mucosal defense against viruses: an in vitro measles virus model," Journal of Virology, vol. 76, No. 21, Nov. 2002, pp. 10972-10979.

\* cited by examiner

CATECHIN FUNCTION ENHANCEMENT METHOD

TECHNICAL FIELD

The present invention relates to a functional food product comprising a green tea extract or a catechin and a citrus fruit extract or a flavanone or a glycoside thereof, etc.

BACKGROUND ART

Cancers are now responsible for one third of deaths in Japan, and it is therefore an urgent problem to establish therapeutic means appropriate for cancers. In multiple myeloma, the therapeutic environment is now being improved by introduction of lenalidomide and bortezomib (i.e., a specific inhibitor of proteasomes). On the other hand, however, there are numerous cases where cancer cells have acquired resistance to existing drugs, thereby causing recurrence. For this reason, there has been a need to develop an anticancer agent having a different mechanism of action from conventional drugs. Further, such an anticancer agent can be used in combination with existing therapies if they differ in their dose limiting toxicity (DLT), which allows planning of a more effective therapeutic strategy.

EGCG (epigallocatechin gallate, epigallocatechin-O-gallate), which is one of the major catechins contained in green tea, has been reported to have an anticancer effect (Non-patent Document 1), and a phase II clinical trial has been conducted in patients with chronic lymphocytic leukemia, a type of blood cancer (Non-patent Document 2). In our previous reports, we have elucidated that EGCG exerts an anticancer effect upon binding to its target molecule 67-kDa laminin receptor (67LR) on the cell membrane (Non-patent Documents 3 to 6). This 67LR has been initially found as a protein binding to laminin, a member constituting the basement membrane (Non-patent Document 7). In recent studies, 67LR has been found to show abnormally enhanced expression in cancer cells (Non-patent Document 8), and a strong correlation has been found between 67LR expression and invasion or metastasis (Non-patent Documents 9 to 15). EGCG has been reported to selectively kill only leukemia cells or multiple myeloma cells via the 67LR-mediated mechanism (Non-patent Documents 16 and 17), thus suggesting that EGCG can serve as a molecular targeted agent against 67LR-positive leukemia cells or multiple myeloma cells. However, the lethal effect of EGCG on leukemia cells or multiple myeloma cells is limited (Non-patent Document 2), and hence there has been a strong demand for enhancement of the effect when EGCG is used as an anticancer agent.

PRIOR ART DOCUMENTS

Non-Patent Documents

Non-patent Document 1: Khan N, Afaq F, Saleem M, et al. Targeting multiple signaling pathways by green tea polyphenol (−)-epigallocatechin-3-gallate. Cancer. res., 2006; 66:2500-2505.
Non-patent Document 2: Shanafelt T D, Call T G, and Zent C S, et al. Phase I trial of daily oral Polyphenon E in patients with asymptomatic Rai stage 0 to II chronic lymphocytic leukemia. J. Clin. Oncol., 2009; 27:3808-3814.
Non-patent Document 3: Tachibana H, Koga K, Fujimura Y, et al. A receptor for green tea polyphenol EGCG. Nat. Struct. Mol. Biol., 2004; 11:380-381.
Non-patent Document 4: Umeda D, Tachibana H, Yamada K. Epigallocatechin-3-O-gallate disrupts stress fibers and the contractile ring by reducing myosin regulatory light chain phosphorylatio mediated through the target molecule 67 kDa laminin receptor. Biochem. Biophys. Res. Commun., 2005; 333:628-635.
Non-patent Document 5: Umeda D, Yano S, Yamada K, et al. Involvement of 67-kDa laminin receptor-mediated myosin phosphatase activation in antiproliferative effect of epigallocatechin-3-O-gallate at a physiological concentration on Caco-2 colon cancer cells. Biochem. Biophys. Res. Commun., 2008; 371:172-176.
Non-patent Document 6: Umeda D, Yano S, Yamada K, et al. Green tea polyphenol epigallocatechin-3-gallate (EGCG) signaling pathway through 67-kDa laminin receptor. J. Biol. Chem., 2008; 283:3050-3058.
Non-patent Document 7: Nelson J, McFerran N V, Pivato G, et al. The 67 kDa laminin receptor: structure, function and role in disease. Biosci. Rep., 2008; 28:33-48.
Non-patent Document 8: Cioce V, Castronovo V, and Shmookler B M, et al. Increased expression of the laminin receptor in human colon cancer. J. Natl. Cancer. Inst., 1991; 83:29-36.
Non-patent Document 9: Menard S, Castronovo V, Tagliabue E, et al. New insights into the metastasis-associated 67 kD laminin receptor. J. Cell Biochem., 1997; 67:155-165.
Non-patent Document 10: Menard S, Taqliabue E, Colnaghi M I. The 67 kDa laminin receptor as a prognostic factor in human cancer. Breast Cancer Res. Treat., 1998; 52:137-145.
Non-patent Document 11: Vacca A, Ribatti D, Roncali L, et al. Melanocyte tumor progression is associated with changes in angiogenesis and expression of the 67-kilodalton laminin receptor. Cancer, 1993; 72:455-461.
Non-patent Document 12: Sanjuan X, Fernandez P L, Miguel, et al. Overexpression of the 67-kD laminin receptor correlates with tumour progression in human colorectal carcinoma. J. Pathol., 1996; 179:376-380.
Non-patent Document 13: Chen F X, Qian Y R, Duan Y H, et al. Down-regulation of 67LR reduces the migratory activity of human glioma cells in vitro. Brain Res. Bull, 2009; 79:402-408.
Non-patent Document 14: Fontanini G, Vignati S, Chine S, et al. 67-Kilodalton laminin receptor expression correlates with worse prognostic indicators in non-small cell lung carcinomas. Clin. Cancer Res., 1997; 3:227-231.
Non-patent Document 15: Basolo F, Pollina L, Pacini F, et al. Expression of the Mr 67,000 laminin receptor is an adverse prognostic indicator in human thyroid cancer: an immunohistochemical study. Clin. Cancer Res., 1996; 2:1777-1780.
Non-patent Document 16: Britschgi A, Simon H U, Tobler A, et al. Epigallocatechin-3-gallate induces cell death in acute myeloid leukaemia cells and supports all-trans retinoic acid-induced neutrophil differentiation via death-associated protein kinase 2. Br. J. Haematol., 2010; 149: 55-64.
Non-patent Document 17: Shammas M A, Neri P, Koley H, et al. Specific killing of multiple myeloma cells by (−)-epigallocatechin-3-gallate extracted from green tea: activity and therapeutic implications. Blood, 2006; 108: 2804-2810.

Non-patent Document 18: Kanda H, Tateya S, Tamori Y, et al. MCP-1 contributes to macrophage infiltration into adipose tissue, insulin resistance, and hepatic steatosis in obesity. J. Clin. Invest. 2006; 116(6):1494-1505.

Non-patent Document 19: Byun H, Fujimura Y, Yamada K, et al. TLR4 signaling inhibitory pathway induced by green tea polyphenol epigallocatechin-3-gallate through 67-kDa laminin receptor, J. Immunol., 2010; 185:33-45.

Non-patent Document 20: Yan H, Lamm M E, Bjorling E, Huang Y T. Multiple functions of immunoglobulin A in mucosal defense against viruses: an in vitro measles virus model. Virol. 2002; 76(21):10972-10979.

Non-patent Document 21: Fujimura Y, Yamada K, Tachibana H, A lipid raft-associated 67 kDa laminin receptor mediates suppressive effect of epigallocatechin-3-O-gallate on FcepsilonRl expression, Biochem. Biophys. Res. Commun., 2005; 336:674-681.

Non-patent Document 22: Holy E W, Stampfli S F, Akhmedov A, et al. Laminin receptor activation inhibits endothelial tissue factor expression. J. Mol. Cell Cardiol. 2010; 48:1138-45.

Non-patent Document 23: Santilli G, Piotrowska I, Cantilena S, et al. Polyphenol Enhances the antitumor immune response in neuroblastoma by inactivating myeloid suppressor cells, Clin. Cancer. Res., 2013; 19:1116-1125.

Non-patent Document 24: Gundimeda U, McNeill T1, Fan T K, et al. Green tea catechins potentiate the neuritogenic action of brain-derived neurotrophic factor: Role of 67-kDa laminin receptor and hydrogen peroxide. Biochem. Biophys. Res. Commun. 2014; 445:218-224.

SUMMARY OF THE INVENTION

Problem to be Solved by the Invention

The present invention aims to provide a composition comprising a green tea extract or a catechin and a citrus fruit extract or a flavanone or a glycoside thereof.

Means to Solve the Problem

As a result of extensive and intensive efforts made to solve the problem stated above, the inventors of the present invention have found that a composition comprising a green tea extract or a catechin and a citrus fruit extract or a flavanone or a glycoside thereof has various effects such as an anticancer effect, an anti-amyotrophic effect, an anti-obesity effect, etc. This finding led to the completion of the present invention.

Namely, the present invention is directed to a composition comprising a green tea extract or a catechin and a citrus fruit extract or a flavanone or a glycoside thereof.

The present invention is also directed to a functional food product comprising a green tea extract or a catechin and a citrus fruit extract or a flavanone or a flavanone glycoside.

The present invention is further directed to an agent comprising a green tea extract or a catechin and a citrus fruit extract or a flavanone or a glycoside thereof, wherein the agent is selected from the group consisting of an anticancer agent, an anti-amyotrophic agent, an anti-obesity agent, an anti-inflammatory agent, a cholesterol-lowering agent, a prophylactic agent for thrombosis or cerebral infarction, and an immunostimulatory agent.

The present invention is further directed to an enhancer comprising a citrus fruit extract or a flavanone or a glycoside thereof for enhancement of at least one effect of a green tea extract or a catechin, wherein the at least one effect is selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect.

The present invention is further directed to a method comprising feeding a subject with a composition comprising a green tea extract or a catechin and a citrus fruit extract or a flavanone or a glycoside thereof to enhance at least one effect of the green tea extract or catechin in the subject (except for medical practice on humans), wherein the at least one effect is selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect.

The green tea extract or catechin intended in the present invention is at least one selected from the group consisting of epicatechin, epigallocatechin, epicatechin gallate, gallocatechin gallate, epigallocatechin gallate and methylated catechin.

The citrus fruit extract or flavanone or glycoside thereof intended in the present invention is at least one selected from the group consisting of eriodictyol, naringenin and hesperetin, as well as glycosides thereof.

In a preferred embodiment of the present invention, the green tea extract or catechin is gallocatechin gallate, epigallocatechin gallate or methylated catechin, and the citrus fruit extract or flavanone is eriodictyol.

The composition, food product, agent and enhancer of the present invention have at least one effect selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect.

Effects of the Invention

The present invention enables the provision of a composition comprising a green tea extract or a catechin and a citrus fruit extract or a flavanone or a glycoside thereof. The composition of the present invention is useful as a functional food product or the like intended to provide an anticancer effect, an anti-amyotrophic effect, an anti-obesity effect and other effects.

BRIEF DESCRIPTION OF THE DRAWINGS

HMGCR (3-hydroxy-3-methylglutaryl-CoA reductase): a rate-limiting enzyme in cholesterol synthesis and a target for drug design of lovastatin and other cholesterol-lowering drugs HMGCS (3-hydroxy-3-methylglutaryl-CoA synthase): an enzyme involved in cholesterol synthesis LDLR (low density lipoprotein receptor): a molecule responsible for LDL uptake in the liver

DESCRIPTION OF EMBODIMENTS

Figure 1:
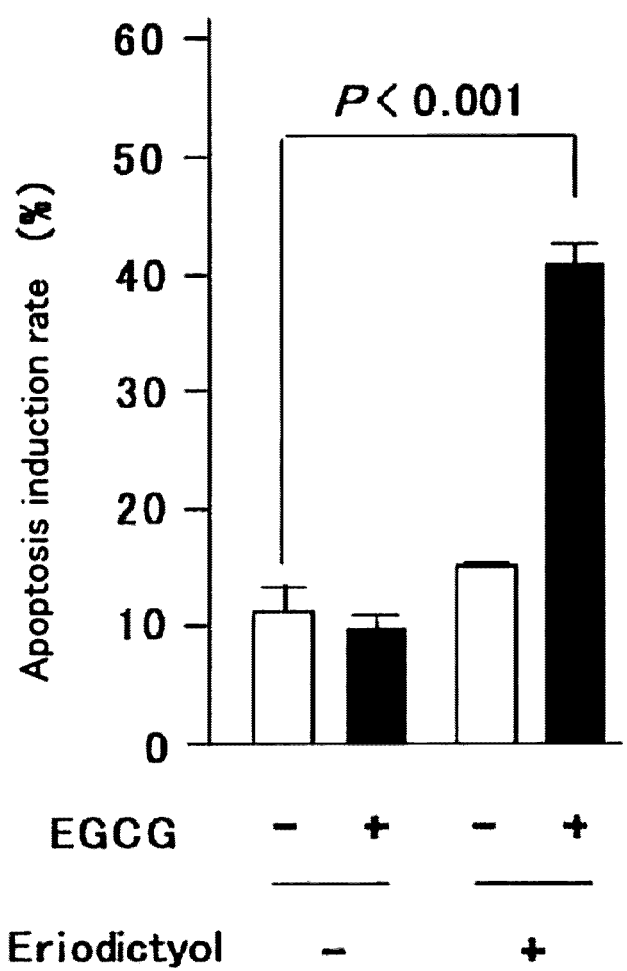
FIG. 1 shows the effect of combination with eriodictyol on the cancer cell apoptosis induction effect of EGCG. Human multiple myeloma cell line U266 was seeded in a 96-well plate ($5 \times 10^4$ cells/mL) and cultured for 96 hours in a medium supplemented with EGCG and eriodictyol (5 µM/L). The cells were collected and then stained with Annexin V Alexa Fluor 488, followed by analysis with a flow cytometer to detect cells where apoptosis was induced.

The present invention will be described in more detail below.

The inventors of the present invention have elucidated that eriodictyol, a kind of polyphenol, enhances the anticancer effect of EGCG. Further, the inventors of the present invention have elucidated that eriodictyol also enhances other effects of EGCG, i.e., an anti-obesity effect, an anti-inflammatory effect, a cholesterol-lowering effect, an anti-thrombotic effect, an immunostimulatory effect and an anti-amyotrophic effect. The inventors of the present invention have also elucidated that eriodictyol or structural analogs thereof or glycosides thereof or eriodictyol-containing naturally occurring products remarkably enhance the effects of EGCG or structural analogs thereof or the effects of EGCG-containing naturally occurring products.

There are reports showing that tea extracts have an anticancer effect, an anti-insulin resistance effect, an anti-inflammatory effect, an antiallergic effect, an anti-amyotrophic effect, a prophylactic effect on arteriosclerosis, an antithrombotic effect, or a prophylactic effect on Alzheimer. Previous studies have shown that EGCG, a green tea polyphenol, develops a wide range of physiological activities through binding to the cell surface protein 67LR. On the other hand, it has been unknown whether any other ingredients would enhance or attenuate the effects of EGCG.

The inventors of the present invention have elucidated that eriodictyol enhances EGCG-induced 67LR activation to thereby promote the anticancer effect, anti-amyotrophic effect, anti-obesity effect, anti-inflammatory effect, anti-thrombotic effect and cholesterol-lowering effect of EGCG under in vivo and in vitro conditions. Moreover, since the obesity-induced increase in MCP-1, which may be reduced by the combined use of eriodictyol and EGCG, is responsible for insulin resistance and hyperlipidemia (Non-patent Document 18), this combined use is useful for the development of food products, medicaments or supplements intended for prevention or treatment of insulin resistance and hyperlipidemia. Further, the inventors of the present invention have elucidated that the combined use of eriodictyol and EGCG increases the blood level of IgA, which is important for immunity. Since IgA is important in the prevention of infections (Non-patent Document 19), the combined use of eriodictyol and EGCG is useful for the development of food products, medicaments or supplements intended for prevention or treatment of infections.

EGCG is known to activate 67LR to thereby exert not only an anticancer effect and an anti-amyotrophic effect, but also an anti-inflammatory effect (Non-patent Document 20), an antiallergic effect (Non-patent Document 21), a prophylactic effect on arteriosclerosis (Non-patent Document 22), an antithrombotic effect (Non-patent Document 22), an immunostimulatory effect (Non-patent Document 23) and a neuron protection effect (Non-patent Document 24).

Thus, when (a1) eriodictyol or a structural analog thereof, i.e., naringenin or hesperetin, (a2) glycosides of these polyphenols which may be metabolized in vivo as these polyphenols, or (a3) food products containing them are used in combination with (b1) EGCG, (b2) methylated EGCG which also serves as a 67LR agonist, as in the case of EGCG, or (b3) food products containing them, these combinations have an anticancer effect, an anti-amyotrophic effect, an anti-obesity effect, an anti-insulin resistance effect, an anti-inflammatory effect, an antiallergic effect, a prophylactic effect on arteriosclerosis, an antithrombotic effect, an anti-neurodegenerative effect, and an anti-inflammatory effect. Thus, the above combinations between (a1), (a2) or (a3) and (b1), (b2) or (b3) are useful as food products, medicaments or supplements intended for prevention or treatment of diseases resulting from the above effects, as exemplified by thrombotic diseases (e.g., pulmonary embolism, DIC, myocardial infarction or cerebral infarction), cancers, amyotrophy, obesity, insulin resistance diseases, inflammatory diseases (e.g., Sjogren's disease and collagenosis), allergic diseases, arteriosclerosis, neurodegenerative diseases (e.g., brain diseases such as Alzheimer and dementia).

(1) Green Tea Extract

The green tea extract intended in the present invention is an extract prepared from tea plant, which is an evergreen tree of the family Theaceae. Green tea plants used in the present invention include tea plants such as *Camellia taliensis, Camellia sinensis* and so on. Examples available for use include tea plant (*Camellia sinensis* (L.) *Kuntze*), Assam tea plant (*Camellia sinensis* (L.) *Kuntze* var *assamica* (J. W. Mast) Kitam.), hybrids between *Camellia sinensis* and *Camellia taliensis*, tea varieties "Yabukita," "Benifuuki," "Benifuji," "Benihomare," "Yaeho," "Surugawase," "Yutakamidori," "Kanayamidori," "Okumusashi," "Seisindaipan," "Seisin oolong," "Ohba oolong," "Benibana," "Benihikari," "Yamakai," "Yamamidori," "Karabeni," "Koushun," "Soufuu," "Fukumidori," "Minekaori," "Benihikari," "Minamikaori," "Izumi," "Fuushun," "Tamamidori," "Yamakai," "Kuritawase," "Shunmei," "Sayamamidori," "Asagiri," "Hokumei," "Tadanishiki," "Asahi," "Sayamakaori," "Meiryoku," "Yamatomidori," "Asatsuyu," "Toyoka," "Natsumidori," "Ujihikari," "Ooiwase," "Gokoh," "Inzatsu 131," "Makinoharawase," "Takachiho," "Komakage," "Samidori," "Komakage," "Hatsumomiji," "Ryoufuu," "Minamisayaka," "Saemidori," "Okuyutaka," "Fujimidori," "Sunrouge" and "Okumidori." Among them, more preferred are "Yabukita," "Benifuuki," "Kanayamidori," "Okumusashi," "Soufuu," "Fuushun," "Tadanishiki" and "Sunrouge." In addition, examples of tea leaves from these tea plants include green tea, refined green tea, coarse green tea, twig green tea, bud green tea, brown rice green tea, broken green tea, powdered green tea, parched green tea, Chinese sweet tea, Pouchong tea, oolong tea, black tea and so on.

As an extraction solvent used to extract tea leaf ingredients from tea plant, water or an organic solvent, or a mixture thereof is used.

Examples of an organic solvent include polar organic solvents such as lower alcohols containing 1 to 4 carbon atoms (e.g., methanol, ethanol, propanol, isopropanol, n-butanol, isobutanol, sec-butanol, tert-butanol) and ketones (e.g., dimethyl ketone, methyl ethyl ketone, acetone, and methyl isobutyl ketone), as well as nonpolar organic solvents such as methyl acetate, ethyl acetate, butyl acetate, or diethyl ether, etc. Further, it is also possible to use any mixture of these polar organic solvents and nonpolar organic solvents, which may be combined as appropriate. Preferred are hot water, ethanol, and hydrous ethanol. The alcohol concentration in hydrous alcohols is 30 v/v % to 90 v/v %, and preferably 40 v/v % to 70 v/v %. In the case of hot water, its temperature is 40° C. to 100° C., and preferably 60° C. to 100° C.

Extraction techniques used to obtain an extract include known techniques such as immersion extraction, heating extraction, continuous extraction, supercritical extraction and so on. The extract thus obtained may then be concentrated in a known manner.

The resulting extract or concentrate or the like may further be purified in a known manner. Purification techniques suitable for this purpose include ultrafiltration, treatment with adsorbent resins, molecular chromatography, partition chromatography, liquid-liquid extraction and so on.

Drying techniques include, but are not limited to, spray drying, freeze drying and so on.

A tea leaf extract contains polyphenols and catechins, etc. A preferred tea extract contains catechin, epicatechin, epigallocatechin, catechin gallate, epicatechin gallate, gallocatechin gallate, epigallocatechin gallate, methylated catechin and the like, more preferably contains epigallocatechin gallate.

Major members of methylated catechin intended in the present invention preferably include epigallocatechin-3-O-(3-O-methyl)gallate (hereinafter referred to as EGCG 3″Me), epicatechin-3-O-(3-O-methyl)gallate (hereinafter referred to as ECG 3″Me), epicatechin-3-O-(4-O-methyl)gallate (hereinafter referred to as ECG 4″Me), epigallocatechin-3-O-(4-O-methyl)gallate (hereinafter referred to as EGCG 4″Me), gallocatechin-3-O-(3-O-methyl)gallate (hereinafter referred to as GCG 3″Me), catechin-3-O-(3-O-methyl)gallate (hereinafter referred to as CG 3″Me), catechin-3-O-(4-O-methyl)gallate (hereinafter referred to as CG 4″Me) or gallocatechin-3-O-(4-O-methyl)gallate (hereinafter referred to as GCG 4″Me), as well as isomerized products thereof.

The content of a green tea extract in the composition will vary depending on the dosage form of the composition or the mode of its administration, but may be determined as appropriate in consideration of the content of a citrus fruit extract or a flavanone described later.

Moreover, in the present invention, the composition may be configured to comprise another catechin different from catechins contained in a tea extract. Examples include synthetic catechins and so on. Synthetic catechins may be obtained in a known manner (Chem. Asian J. 2010, 5, 2231-2248. DOI: 10.1002/asia.201000372).

(2) Citrus Fruit Extract

The citrus fruit extract intended in the present invention is a product extracted from a citrus fruit, which contains flavanones, etc. Examples of a citrus fruit include the following.

The genus Citrus:

orange, grapefruit, *Citrus junos*, bitter orange, *Citrus sphaerocarpa, Citrus sudachi, Citrus yuko* hort.ex Tanaka, Yukou (a native Japanese citrus), *Citrus depressa*, lemon, lime, *Citrus natsudaidai, Citrus hassaku, Citrus iyo, Citrus grandis*, mandarin orange, satsuma mandarin, *Cirus reticulata, Citrus tachibana, Citrus kinokuni*, Valencia orange, navel orange, blood orange, Jaffa orange, bergamot orange, Chinotto orange, etc.

In addition to the above citrus fruits of the genus Citrus, trifoliate oranges, kumquats and others may also be used.

As an extraction solvent used to extract a citrus fruit, water or an organic solvent, or a mixture thereof is used, as in the case described above.

Examples of an organic solvent include polar organic solvents such as lower alcohols containing 1 to 4 carbon atoms (e.g., methanol, ethanol, propanol, isopropanol, n-butanol, isobutanol, sec-butanol, tert-butanol) and ketones (e.g., dimethyl ketone, methyl ethyl ketone, acetone, and methyl isobutyl ketone), as well as nonpolar organic solvents such as methyl acetate, ethyl acetate, butyl acetate, or diethyl ether, etc. Preferred is water or ethanol. Further, it is also possible to use any mixture of these polar organic solvents and nonpolar organic solvents, which may be combined as appropriate.

Extraction techniques used to obtain an extract include known techniques such as immersion extraction, heating extraction, continuous extraction, supercritical extraction and so on. The extract thus obtained may then be concentrated in a known manner.

The resulting extract or concentrate or the like may further be purified in a known manner. Purification techniques suitable for this purpose include ultrafiltration, treatment with adsorbent resins, molecular chromatography, partition chromatography, liquid-liquid extraction and so on.

A citrus fruit extract contains flavanones. A preferred citrus fruit extract contains eriodictyol, naringenin and hesperetin and glycosides thereof (i.e., eriodictyol glycoside, naringenin glycoside, hesperetin glycoside) and the like, more preferably contains eriodictyol.

Moreover, in the present invention, the composition may be configured to comprise another flavanone different from flavanones contained in a citrus fruit extract. Examples include synthetic flavanones, transglycosylated compounds of flavanones each being linked with a sugar molecule, etc., as exemplified by synthetic eriodictyol, synthetic naringenin and synthetic hesperetin, which may be used either alone or in combination. Synthetic eriodictyol, synthetic naringenin and synthetic hesperetin may be obtained in a known manner (European J Org Chem., 2012(3): 449-462. doi: 10.1002/ejoc.201101228).

Moreover, the content of a citrus fruit extract in the composition will vary depending on the dosage form of the composition or the mode of its administration.

In the composition of the present invention, the ratio between a tea extract or a catechin and a citrus fruit extract or a flavanone or a glycoside thereof (tea extract/citrus fruit extract, mass ratio) will vary depending on the degree of their concentration, but the ratio may preferably be set to 100 to 0.01. Moreover, the content of a tea extract or a catechin and the content of a citrus fruit extract or a flavanone or a glycoside thereof in the composition may be set as appropriate within the above range of mass ratio. For example, the content of a tea extract or a catechin is 90% by weight to 0.001% by weight, and preferably 30% by weight to 0.01% by weight, while the content of a flavanone or a glycoside thereof is 90% by weight to 0.001% by weight, and preferably 20% by weight to 0.01% by weight.

(3) Composition

In addition to the ingredients described above, the composition of the present invention may further comprise a carrier acceptable for use in food products and any other known or well-known additives.

Examples of the above additives include those commonly used in medicaments or food products, such as excipients, binders, lubricants, disintegrants, coloring agents, correctives, emulsifiers, surfactants, solubilizers, suspending agents, isotonizing agents, buffering agents, antiseptics, antioxidants, stabilizers, absorbefacients and so on, which may be used in combination as appropriate, if desired.

The composition of the present invention may be in any of liquid, solid, powder and gel forms, and the composition of the present invention may be formulated into any oral dosage form, such as tablets, powders, capsules (hard capsules, soft capsules), granules, pills, solutions, syrups and so on. These formulations may be prepared in a standard manner.

If the composition is in a solution form, carriers preferred for use include water and other aqueous media.

Likewise, if the composition is in a solid form, ingredients to be added include excipients such as crystalline cellulose, magnesium stearate, calcium stearate and so on, as well as expanders such as corn starch, alginic acid and so on.

Moreover, compounds required for formulation into a powder, solid or solution dosage form include erythritol, maltitol, hydroxypropyl cellulose, kaolin, talc and so on.

The composition of the present invention has at least one effect selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect. Thus, the above composition can be used as an anticancer agent, an anti-amyotrophic agent, an anti-obesity agent, an anti-inflammatory agent, a cholesterol-lowering agent, a prophylactic agent for thrombosis or cerebral infarction, or an immunostimulatory agent. In the above respective agents, the preparation of a tea extract or a catechin and a citrus fruit extract or a flavanone and the content of these respective ingredients are the same as described above.

Subjects to be fed with the composition of the present invention are not limited in any way but include not only humans, but also non-human mammals, as exemplified by laboratory animals (e.g., mice, rats, guinea pigs, rabbits), domestic animals (e.g., cows, horses, pigs, goats), pet animals (e.g., dogs, cats and other pets), etc. The composition of the present invention can be expected to prevent or treat cancers, amyotrophy (e.g., amyotrophic lateral sclerosis (ALS)), inflammatory diseases, thrombosis or cerebral infarction, hyperlipidemia and infections, or to improve lifestyle-related diseases and obesity.

(4) Food Product

The food product of the present invention comprises a tea extract or a catechin and a citrus fruit extract or a flavanone or a glycoside thereof, and is particularly used as a functional food product, a supplement or the like intended to provide at least one effect selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect.

Food products (particularly functional food products) containing the composition of the present invention may be in any form, including supplements (i.e., powders, granules, soft capsules, hard capsules, tablets, chewable tablets, rapidly disintegrating tablets), as well as beverages (e.g., tea beverages, carbonated beverages, lactic acid beverages, sports drinks), confectionery (e.g., gums, chocolates, cookies, candies), oils, edible fat and oil products (e.g., mayonnaise, dressings, butter), seasonings (e.g., ketchups, sauces), fluid diets, dairy products (e.g., cow milk, yogurt, cheese), bakery products, noodles (e.g., white wheat noodles, buckwheat noodles, Chinese noodles, pasta, Hiyamugi (Japanese vermicelli), rice vermicelli), etc. However, the food product of the present invention is not limited only to these forms.

Subjects to be fed with the food product of the present invention are the same as described above, and are not limited in any way but include not only humans, but also non-human mammals, as exemplified by laboratory animals (e.g., mice, rats, guinea pigs, rabbits), domestic animals (e.g., cows, horses, pigs, goats), pet animals (e.g., dogs, cats and other pets), etc.

In the food product of the present invention, the content of a tea extract or a catechin and the content of a citrus fruit extract or a flavanone or a glycoside thereof are the same as described above in the composition section and may be set as appropriate within the range of mass ratio mentioned above. For example, the content of a tea extract or a catechin is 90% by weight to 0.001% by weight, and preferably 30% by weight to 0.01% by weight, while the content of a flavanone or a glycoside thereof is 90% by weight to 0.001% by weight, and preferably 20% by weight to 0.01% by weight.

(4) Enhancer

As described above, the inventors of the present invention have elucidated that eriodictyol enhances the effects of EGCG, i.e., an anticancer effect, an anti-obesity effect, an anti-inflammatory effect, a cholesterol-lowering effect, an antithrombotic effect, an immunostimulatory effect and an anti-amyotrophic effect.

Thus, the present invention provides an enhancer comprising a citrus fruit extract or a flavanone or a glycoside thereof for enhancement of at least one effect of a green tea extract or a catechin, wherein the at least one effect is selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect. Moreover, the present invention also provides a method comprising feeding a subject with a composition comprising a green tea extract or a catechin and a citrus fruit extract or a flavanone or a glycoside thereof to enhance at least one effect of the green tea extract or catechin in the subject, wherein the at least one effect is selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect (provided that medical practice on humans can be excluded).

When used as an enhancer or in an enhancement method, a citrus fruit extract or a flavanone or a glycoside thereof may also be applied in the same manner as descried above in the composition section.

Subjects intended in the enhancer and enhancement method of the present invention are the same as described above, and are not limited in any way but include not only humans, but also non-human mammals, as exemplified by laboratory animals (e.g., mice, rats, guinea pigs, rabbits), domestic animals (e.g., cows, horses, pigs, goats), pet animals (e.g., dogs, cats and other pets), etc.

The present invention will be further described in more detail by way of the following examples, although the present invention is not limited only to these examples.

EXAMPLES

Experimental Procedures

Effect of Combination with Eriodictyol on the Cancer Cell Apoptosis Induction Effect of Egcg Human multiple myeloma cell line U266 was subcultured and maintained in RPMI 1640 medium supplemented with 10% fetal bovine serum (FCS) under conditions of 37° C. and water vapor-saturated 5% $CO_2$. The cells were maintained in the logarithmic growth phase. The RPMI 1640 medium used for culture was prepared as follows: per liter of ultrapure water, RPMI 1640 medium (10.4 g), HEPES (2.38 g), injectable penicillin G potassium (100,000 units), streptomycin sulfate injectable (100 mg) and NaHCO$_3$ (2.0 g) were suspended and then filter-sterilized.

Then, the RPMI 1640 medium was supplemented with FCS and used for cell culture. To examine the apoptosis induction effect on human multiple myeloma cell line U266 produced upon combination of EGCG and eriodictyol, double staining was performed with Annexin V and PI. For use as a propidium iodide (PI) stain solution, PI (Sigma) was suspended in PBS at a concentration of 50 µg/mL.

Per liter of ultrapure water, NaCl (8.0 g), KCl (0.2 g), Na$_2$HPO$_4$ (1.15 g) and KH$_2$PO$_4$ (0.2 g) were dissolved to prepare PBS, which was then sterilized in an autoclave. The Annexin V binding buffer used was prepared to contain 10 mM HEPES, 140 mM NaCl and 2.5 mM CaCl$_2$ (Wako), adjusted to pH 7.4 and subjected to filter sterilization. The eriodictyol used was adjusted to 5 mM with 100% dimethyl sulfoxide (DMSO) and stored at −30° C. EGCG (purchased from Sigma) was adjusted to 5 mM with ultrapure water and stored at −30° C. U266 adjusted to 5×10$^4$ cells/mL (U266) in RPMI 1640 containing 1% FCS, SOD (5 U/mL) and catalase (200 U/mL) was seeded in a 96-well plate and cultured for 96 hours in the presence of EGCG and eriodictyol added at a final concentration of 5 µM each.

Then, the fully suspended cell culture was centrifuged at 300×g for 5 minutes to remove the supernatant, and then suspended with the Annexin V binding buffer, counted with a hemacytometer, centrifuged again at 300×g for 5 minutes and then suspended with the Annexin V binding buffer. To 100 µL of this cell suspension, 5 µL of Annexin V Alexa Fluor 488 conjugate (Invitrogen) was added and the PI stain solution (2 µL) was further added, followed by standing at room temperature for 15 minutes. Then, the Annexin V binding buffer (400 µL) was added from the top, followed by measurement with a flow cytometer FACS Caliber (Becton, Dickinson and Company). After compensation, the Annexin V Alexa Fluor 488 conjugate was measured at FL 1 and cells determined to be positive were regarded as apoptotic cells.

Anticancer Effect in Tumor-Implanted Mice Upon Combined Use of EGCG and Eriodictyol After female balb/c mice at 5 weeks of age were preliminarily kept for 2 weeks, a cell suspension of mouse multiple myeloma cell line MPC-11 suspended at 5×10$^6$ cells/mL in RPMI medium was implanted by subcutaneous injection in a volume of 200 µL into the right dorsal region of each mouse under anesthesia with isoflurane (Mylan N.V., Tokyo, Japan). At 11 days after implantation, the mice were administered once every 2 days with EGCG (15 mg/kg i.p.) and eriodictyol (15 mg/kg i.p.) and measured every 2 days for their tumor volume with a caliper. The tumor volume was calculated according to the following equation.

$$\text{<Tumor volume (mm}^3\text{)=(short axis)}^2\text{×long axis×0.5>}$$

From an ethical standpoint, the mice whose tumor volume exceeded 4000 mm$^3$ were sacrificed by cardiac puncture under anesthesia with isoflurane (Mylan N.V., Tokyo, Japan).

Hepatotoxicity in Tumor-Implanted Mice Upon Combination of EGCG and Eriodictyol

After female balb/c mice at 5 weeks of age were preliminarily kept for 2 weeks, a cell suspension of mouse multiple myeloma cell line MPC-11 suspended at 5×10$^6$ cells/mL in RPMI medium was implanted by subcutaneous injection in a volume of 200 µL into the right dorsal region of each mouse under anesthesia with isoflurane (Mylan N.V., Tokyo, Japan). At 11 days after implantation, the mice were administered once every 2 days with EGCG (15 mg/kg i.p.) and eriodictyol (15 mg/kg i.p.). The mice were sacrificed by cardiac puncture under anesthesia. The collected blood samples were allowed to stand at 37° C. for 2 hours to cause coagulation and then centrifuged at 4° C. at 2000×g for 15 minutes to collect serum fractions. The resulting serum fractions were measured using a kit (Wako) for serum aspartate aminotransferase (AST) and alanine aminotransferase (ALT) activities, which are indicative of hepatotoxicity.

Effect of the Combined Product of EGCG and Eriodictyol on Disuse Amyotrophy

Male C57BL/6J mice at 12 weeks of age were divided into 5 groups such that the average body weight was equal in all groups, i.e., a GR (ground) group, a TS (tail suspension) group, an EGCG group, an eriodictyol group, and an EGCG+eriodictyol group. From the beginning of grouping, the GR and TS groups received physiological saline, the EGCG group received EGCG and the eriodictyol group received eriodictyol (5 mg/kg) by intragastric administration, while the EGCG+eriodictyol group received EGCG and eriodictyol (5 mg/kg) by intragastric administration through a sonde. For 7 days from the beginning of grouping, all the groups were kept under normal conditions, and the TS, EGCG, eriodictyol, and EGCG+eriodictyol groups were then subjected to a tail suspension test. After the tail suspension test for 10 days (at 17 days after initiation of the experiment), all the mice were sacrificed by abdominal aortic puncture under isoflurane anesthesia, and the quadriceps femoris was excised from each mouse and measured for its weight. Each sample was administered daily throughout the experimental period.

Effect of Combined Intake of a Green Tea Extract and Eriodictyol on High-Fat High-Sucrose (HF/HS) Diet-Fed Mice Male C57BL/6J mice at 12 weeks of age were preliminarily kept for 1 week and then divided into 5 groups such that the average body weight was equal in all groups, i.e., a control (AIN-93G-based diet) group, a HF/HS (high-fat high-sucrose diet) group, a Yabukita (0.2%) (HF/HS+Yabukita) group, an eriodictyol (HF/HS+eriodictyol) group, and a Yabukita+eriodictyol (HF/HS+Yabukita+eriodictyol) group. A feed supplemented with Yabukita (0.2%) and eriodictyol (0.45 g/kg diet) was given to the mice. The feed was given in an amount of 4 g/day and the mice were kept for 8 weeks under ad libitum drinking conditions. After being fasted for 16 hours, the mice were sacrificed by abdominal aortic puncture under isoflurane anesthesia. The collected blood samples were allowed to stand at 37° C. for 2 hours to cause coagulation and then centrifuged at 4° C. at 2000×g for 15 minutes to collect serum fractions. The values of serum total cholesterol and LDL were measured. Fat tissues were treated with TRIzol and cDNAs were synthesized, followed by real-time PCR to measure the mRNA expression level of MCP-1.

Effect of Combined Intake of a Green Tea Extract and Eriodictyol on Cholesterol Metabolism-Related Gene Expression in the Liver of High-Fat High-Sucrose (HF/HS) Diet-Fed Mice Male C57BL/6J mice at 12 weeks of age were preliminarily kept for 1 week and then divided into 5 groups such that the average body weight was equal in all groups, i.e., a control (AIN-93G-based diet) group, a HF/HS (high-fat high-sucrose diet) group, a Yabukita (0.2%) (HF/HS+Yabukita) group, an eriodictyol (HF/HS+eriodictyol) group, and a Yabukita+eriodictyol (HF/HS+Yabukita+eriodictyol) group. A feed supplemented with Yabukita (0.2%) and eriodictyol (0.45 g/kg diet) was given to the mice. The feed was given in an amount of 4 g/day and the mice were kept for 8 weeks under ad libitum drinking conditions. After being fasted for 16 hours, the mice were sacrificed by abdominal aortic puncture under isoflurane anesthesia. Liver tissues were treated with TRIzol and cDNAs were synthesized, followed by real-time PCR to measure the mRNA expression levels of 3-hydroxy-3-methyl-glutaryl-CoA reductase (HMGCR), 3-hydroxy-3-methylglutaryl-CoA synthase (HMCGS) and low density lipoprotein receptor (LDLR).

Effect of Combined Intake of a Green Tea Extract and Eriodictyol on Antithrombotic Factor Production Male C57BL/6J mice at 12 weeks of age were preliminarily kept for 1 week and then divided into 4 groups such that the average body weight was equal in all groups, i.e., a HF/HS (high-fat high-sucrose diet) group, a Yabukita (0.2%) (HF/HS+Yabukita) group, an eriodictyol (HF/HS+eriodictyol) group, and a Yabukita+eriodictyol (HF/HS+Yabukita+eriodictyol) group. A feed supplemented with Yabukita (0.2%) and eriodictyol (0.45 g/kg diet) was given to the mice. The feed was given in an amount of 4 g/day and the mice were kept for 8 weeks under ad libitum drinking conditions. After being fasted for 16 hours, the mice were sacrificed by abdominal aortic puncture under isoflurane anesthesia. The collected blood samples were allowed to stand at 37° C. for 2 hours to cause coagulation and then centrifuged at 4° C. at 2000×g for 15 minutes to collect serum fractions. The serum level of tissue factor pathway inhibitor (TFPI), an antithrombotic factor, was measured by ELISA assay.

Effect of Combined Intake of a Green Tea Extract and Eriodictyol on the Serum Level of IgA Male C57BL/6J mice at 12 weeks of age were preliminarily kept for 1 week and then divided into 4 groups such that the average body weight was equal in all groups, i.e., a HF/HS (high-fat high-sucrose diet) group, a Yabukita (0.2%) (HF/HS+Yabukita) group, an eriodictyol (HF/HS+eriodictyol) group, and a Yabukita+eriodictyol (HF/HS+Yabukita+eriodictyol) group. A feed supplemented with Yabukita (0.2%) and eriodictyol (0.45 g/kg diet) was given to the mice. The feed was given in an amount of 4 g/day and the mice were kept for 8 weeks under ad libitum drinking conditions. After being fasted for 16 hours, the mice were sacrificed by abdominal aortic puncture under isoflurane anesthesia. The collected blood samples were allowed to stand at 37° C. for 2 hours to cause coagulation and then centrifuged at 4° C. at 2000×g for 15 minutes to collect serum fractions. The serum level of IgA was measured by ELISA assay.

Effect of Combination with Eriodictyol, an Eriodictyol-Related Substance (Naringenin, Hesperetin) or an Eriodictyol-Containing Food Product Extract on the Cancer Cell Death Induction Activity of EGCG, EGCG 3"Me or a Green Tea Extract Human multiple myeloma cell line U266 was subcultured and maintained in RPMI 1640 medium supplemented with 10% FCS under conditions of 37° C. and water vapor-saturated 5% $CO_2$. The cells were maintained in the logarithmic growth phase. The RPMI 1640 medium used for culture was prepared as follows: per liter of ultrapure water, RPMI 1640 medium (10.4 g), HEPES (2.38 g), injectable penicillin G potassium (100,000 units), streptomycin sulfate injectable (100 mg) and $NaHCO_3$ (2.0 g) were suspended and then filter-sterilized.

The lemon peel extract used in the experiment was prepared as follows. Peels (100 g) were collected with a grater from 6 lemons and 100% EtOH (100 mL) was added thereto, followed by mashing with a mortar. The mashed mixture was further strained through gauze to remove fibers and then filtered by gravity using a #1 paper filter and a funnel to remove precipitates, followed by centrifugation at 12000×g to collect the supernatant. The resulting ethanol extract of lemon was evaporated with an evaporator to volatilize the solvent, thereby obtaining an ethanol-extracted lemon fraction. This ethanol-extracted lemon fraction was dissolved again in DMSO to give a lemon extract. Then, U266 adjusted to $5\times10^4$ cells/mL in RPMI 1640 containing 1% FCS, SOD (5 U/mL) and catalase (200 U/mL) was seeded in a 96-well plate and cultured for 96 hours in the presence of eriodictyol, an eriodictyol-related substance (naringenin, hesperetin) or an eriodictyol-containing food product on the cancer cell death induction activity of EGCG, EGCG 3"Me or a green tea extract. After culture, viable cells were counted by trypan blue assay.

67LR Dependency of Eriodictyol-Induced EGCG Activity Enhancement

Human multiple myeloma cell line U266 was subcultured and maintained in RPMI 1640 medium supplemented with 10% FCS under conditions of 37° C. and water vapor-saturated 5% $CO_2$. The cells were maintained in the logarithmic growth phase. The RPMI 1640 medium used for culture was prepared as follows: per liter of ultrapure water, RPMI 1640 medium (10.4 g), HEPES (2.38 g), injectable penicillin G potassium (100,000 units), streptomycin sulfate injectable (100 mg) and $NaHCO_3$ (2.0 g) were suspended and then filter-sterilized. U266 adjusted to $5\times10^4$ cells/mL in RPMI 1640 containing 1% FCS, SOD (5 U/mL) and catalase (200 U/mL) was seeded in a 96-well plate, immediately followed by addition of anti-67LR monoclonal antibody MLuc5 (abcam) at a final concentration of 20 μg/mL. After 3 hours, eriodictyol and EGCG were added at a final concentration of 5 μM each. Viable cells were counted by ATPlite One Step (Perkin Elmer).

Enhancement Effect of Eriodictyol on the Ability of EGCG to Induce Akt Activation After female balb/c mice at 5 weeks of age were preliminarily kept for 2 weeks, a cell suspension of mouse multiple myeloma cell line MPC-11 suspended at $5\times10^6$ cells/mL in RPMI medium was implanted by subcutaneous injection in a volume of 200 μL into the right dorsal region of each mouse. At 11 days after implantation, the mice were administered with EGCG (15 mg/kg i.p.) and eriodictyol (15 mg/kg i.p.) and then sacrificed after 6 hours to excise their tumors. At 11 days after implantation, the mice were administered with EGCG (15 mg/kg i.p.) and eriodictyol (15 mg/kg i.p.). After 6 hours, the mice were sacrificed. After tumors were excised and treated into lysates, the collected samples (1 mg/mL protein lysate 20 μL) were each mixed sequentially with a kinase assay buffer (20 μL), a biotinylated Akt substrate WS (10 μL), $dH_2O$ (50 μL) and an ATP/$MgCl_2$ mix (20 μL) and then incubated at 37° C. for 45 minutes, followed by addition of a kinase stop solution (10 μP. Then, the samples were dispensed in 80 μL volumes into wells of a streptavidin-coated 96-well plate and allowed to stand at 30° C. for 60 minutes. The plate was then washed three times and a phosphoserine detection antibody was added in a volume of 100 μL to each well, followed by standing at 30° C. for 60 minutes. The plate was then washed three times and an HRP-antibody conjugate was added in a volume of 100 μL to each well, followed by standing at 30° C. for 60 minutes. The plate was then washed three times and a TMB solution serving as a substrate was added in a volume of 100 μL to each well. After the plated was allowed to stand at 30° C. for 20 minutes, a stop solution was added in a volume of 100 µL to each well and the absorbance at 450 nm was measured with a plate reader.

Enhancement Effect of Eriodictyol on EGCG-Induced Activation of the 67LR-Dependent Cancer Cell Death Induction Pathway (Acid Sphingomyelinase Activation)

After female balb/c mice at 5 weeks of age were preliminarily kept for 2 weeks, a cell suspension of mouse multiple myeloma cell line MPC-11 suspended at $5 \times 10^6$ cells/mL in RPMI medium was implanted by subcutaneous injection in a volume of 200 µL into the right dorsal region of each mouse. At 11 days after implantation, the mice were administered with EGCG (15 mg/kg i.p.) and eriodictyol (15 mg/kg i.p.) and then sacrificed after 6 hours. Tumors were excised and treated into lysates, and then centrifuged. The supernatants were each adjusted with PBS to 2 mg protein/mL and then dispensed in 20 µL volumes into Eppendorf tubes, followed by addition of a substrate mixture (2 µL of BODIPY-C12-SM, 10 µL of 10% Triton, 20 µL of 1 M sodium acetate pH 4.5, and 78 µL of $dH_2O$) in a volume of 8 µL to each tube. The tubes were tapped for mixing and then flushed, followed by incubation at 37° C. for 8 hours. Further, a stop solution (chloroform $CHCl_3$:MeOH=2:1) was added in a volume of 60 µL to each tube, and the samples were each spotted in a volume of 10 µL onto a thin-layer chromatography (TLC) plate, which had been activated in a desiccator, and then developed with a developing solvent ($dH_2O$:MeOH:chloroform $CHCl_3$=8:35:60). The acid sphingomyelinase activity was measured by TLC assay (n=5 S.E.M.).

Enhancement Effect of Eriodictyol on the 67LR-Dependent Cancer Cell Death Activity (Caspase-3 Activity) of EGCG After female balb/c mice at 5 weeks of age were preliminarily kept for 2 weeks, a cell suspension of mouse multiple myeloma cell line MPC-11 suspended at $5 \times 10^6$ cells/mL in RPMI medium was implanted by subcutaneous injection in a volume of 200 µL into the right dorsal region of each mouse. At 11 days after implantation, the mice were administered once every 2 days with EGCG (15 mg/kg i.p.) and eriodictyol (15 mg/kg i.p.) and then sacrificed after 6 hours. Tumors were excised and tissue sections were prepared therefrom, followed by immunohistological staining to determine the number of cells where caspase-3 was activated.

Statistics

For statistical processing of the experimental results, Tukey's test was used and P<0.05 was considered statistically significant.

Example 1

Effect of Combination with Eriodictyol on the Cancer Cell Apoptosis Induction Effect of EGCG (FIG. 1)

To evaluate the effect of eriodictyol on the cancer cell apoptosis induction effect of EGCG, human multiple myeloma cell line U266 was adjusted to $5 \times 10^4$ cells/mL and seeded in a 96-well plate, and then cultured for 96 hours in the presence of EGCG and eriodictyol added at a final concentration of 5 µM each. After culture for 96 hours, the Annexin V Alexa Fluor 488 conjugate (Invitrogen) was added in a volume of 5 µL. The PI stain solution (2 µL) was added and the cells were allowed to stand at room temperature for 15 minutes. Then, the Annexin V binding buffer (400 µL) was added and the number of cells where apoptosis was induced was measured with a flow cytometer.

As a result, eriodictyol was found to enhance the apoptosis induction effect of EGCG.

Example 2

Figure 2:
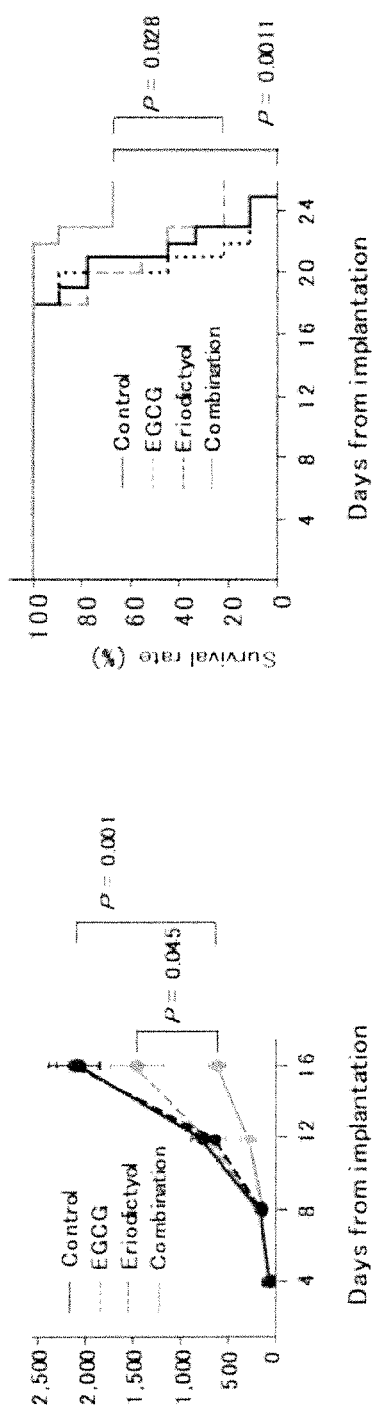
FIG. 2 shows an anticancer effect in tumor-implanted mice upon combined use of EGCG and eriodictyol. Multiple myeloma cell line MPC-11 was subcutaneously injected into the right dorsal region of Balb/c mice, followed by administration of EGCG (15 mg/kg) and eriodictyol (15 mg/kg) once every 2 days. The mice were measured for their tumor volume and survival period after the initiation of administration.

Anticancer Effect in Tumor-Implanted Mice Upon Combined Use of EGCG and Eriodictyol (FIG. 2)

To evaluate the anticancer effect upon combination of EGCG and eriodictyol, Balb/c mice were preliminarily kept for 2 weeks and a cell suspension of mouse multiple myeloma cell line MPC-11 suspended at $5 \times 10^6$ cells/mL in RPMI medium was then subcutaneously injected into the right dorsal region of each mouse. After confirmation of tumor engraftment, the mice were administered once every 2 days with EGCG (15 mg/kg i.p.) and eriodictyol (15 mg/kg i.p.) and measured for their tumor volume. As a result, the combined use of eriodictyol and EGCG was found not only to remarkably inhibit tumor growth, but also to significantly prolong the survival period.

Example 3

Figure 3:
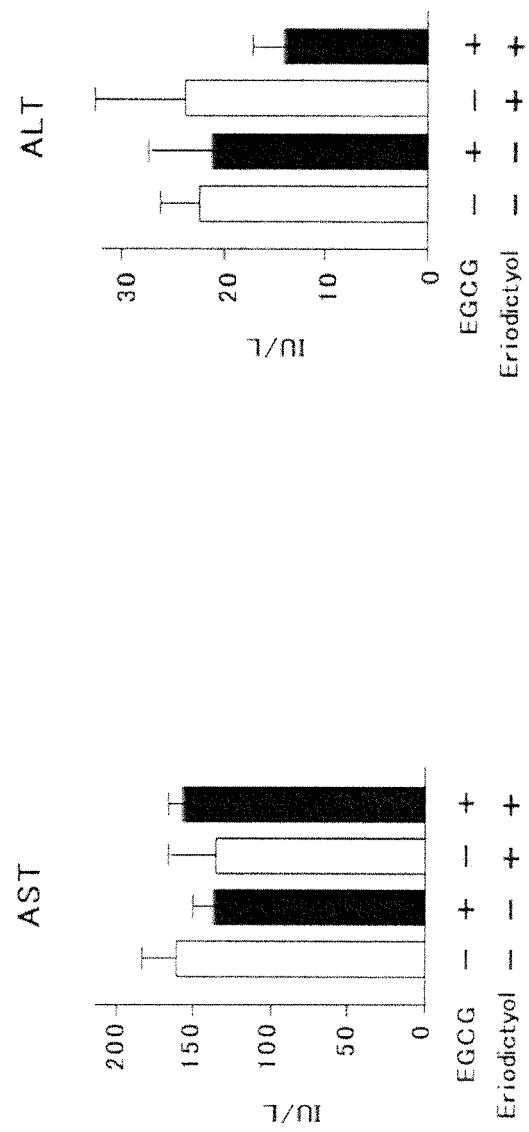
FIG. 3 shows hepatotoxicity in tumor-implanted mice upon combination of EGCG and eriodictyol. Multiple myeloma cell line MPC-11 was subcutaneously injected into the right dorsal region of Balb/c mice, followed by administration of EGCG (15 mg/kg) and eriodictyol (15 mg/kg) once every 2 days. For determination of hepatotoxicity, the mice were measured for their serum aspartate aminotransferase (AST) and alanine aminotransferase (ALT) activities.

Hepatotoxicity in Tumor-Implanted Mice Upon Combination of EGCG and Eriodictyol (FIG. 3)

Mice which had been implanted with mouse multiple myeloma cell line MPC-11 were administered once every 2 days with EGCG (15 mg/kg i.p.) and eriodictyol (15 mg/kg i.p.). The mice were sacrificed and measured for their serum aspartate aminotransferase (AST) and alanine aminotransferase (ALT) activities.

As a result, the combination of EGCG and eriodictyol did not induce increases in AST and ALT levels, thus indicating that this combination showed no hepatotoxicity.

Example 4

Figure 4:
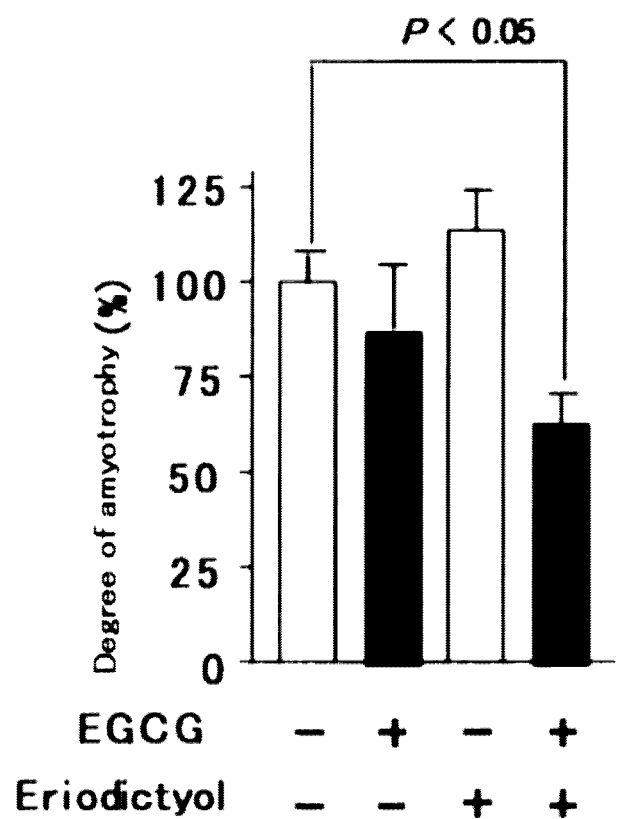
FIG. 4 shows the effect of the combined product of EGCG and eriodictyol on disuse amyotrophy. C57BL/6J mice were administered once a day with EGCG or eriodictyol (5 mg/kg). At 7 days after the initiation of administration, the mice started to undergo tail suspension. At 10 days after the initiation of tail suspension, the mice were sacrificed and measured for their quadriceps femoris weight.

Effect of the Combined Product of EGCG and Eriodictyol on Disuse Amyotrophy (FIG. 4)

EGCG and eriodictyol were examined for their effect on tail suspension test-induced disuse amyotrophy in mice. C57BL/6J mice were intragastrically administered once a day with water or each sample through a sonde. At 7 days after the initiation of administration, a tail suspension test was started. At 10 days after starting the tail suspension test, the mice were sacrificed by abdominal aortic puncture under isoflurane anesthesia, and the quadriceps femoris was excised from each mouse and measured for its weight.

As a result, EGCG and eriodictyol were found to have no effect on amyotrophy when administered alone, whereas amyotrophy was suppressed in the mice administered with EGCG and eriodictyol in combination. These results indicated that the combined use of EGCG and eriodictyol had a suppressive effect on amyotrophy.

Example 5

Figure 5:
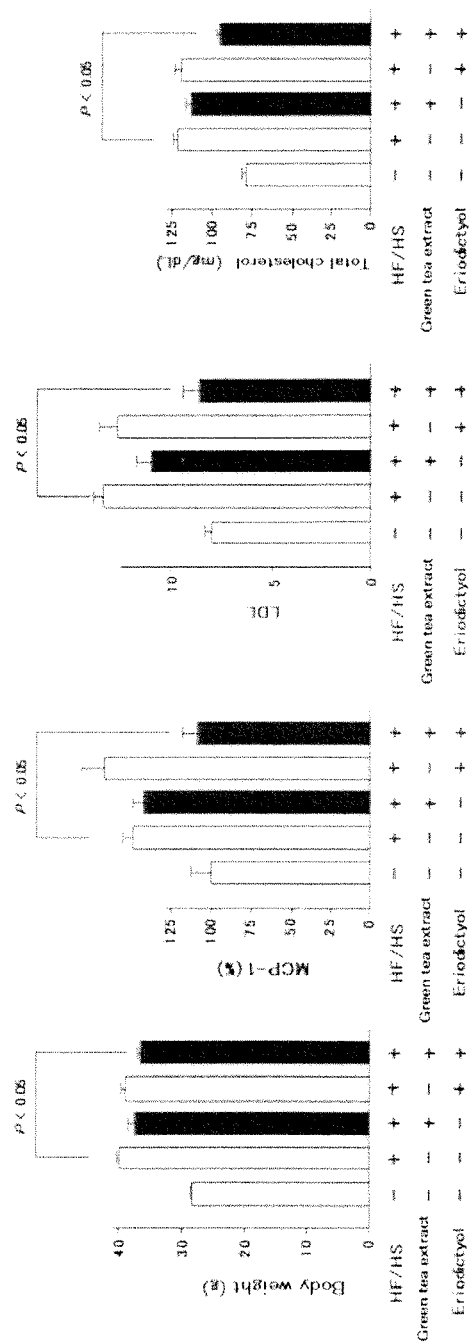
FIG. 5 shows the effect of combined intake of a green tea extract and eriodictyol on high-fat high-sucrose (HF/HS) diet-fed mice. C57BL/6J mice were fed with a diet supplemented with a green tea extract (0.2%) and eriodictyol (0.45 g/kg diet). After being kept for 8 weeks, the mice were measured for their respective values of body weight, serum total cholesterol and LDL. The mice were also measured for the mRNA expression level of MCP-1 in their fat tissue by real-time PCR assay.

Effect of Combined Intake of a Green Tea Extract and Eriodictyol on High-Fat High-Sucrose (HF/HS) Diet-Fed Mice (FIG. 5)

Yabukita and eriodictyol were examined for their effect on obesity in high-fat high-sucrose diet-fed obese model mice. Male C57BL/6J mice at 12 weeks of age were preliminarily kept for 1 week and then divided into the respective groups such that the average body weight was equal in all groups. Each feed was given in an amount of 4 g/day and the mice were kept for 8 weeks under ad libitum drinking conditions. After being measured for their body weight, the mice were fasted for 16 hours and then sacrificed by abdominal aortic puncture under isoflurane anesthesia. Blood samples collected by puncture were allowed to stand at 37° C. for 2 hours to cause coagulation and then centrifuged at 4° C. at 2000×g for 15 minutes to collect serum fractions. The values of serum total cholesterol and LDL were measured. Fat tissues were treated with TRIzol and cDNAs were synthesized, followed by real-time PCR to measure the mRNA expression level of MCP-1.

As a result, the group receiving Yabukita or eriodictyol alone showed no effect on high-fat high-sucrose diet-induced increases in body weight, fat tissue MCP-1 expression level, LDL value and serum cholesterol value, whereas suppressive effects on increases in all of these values were observed in the group receiving Yabukita and eriodictyol in combination.

Example 6

Figure 6:
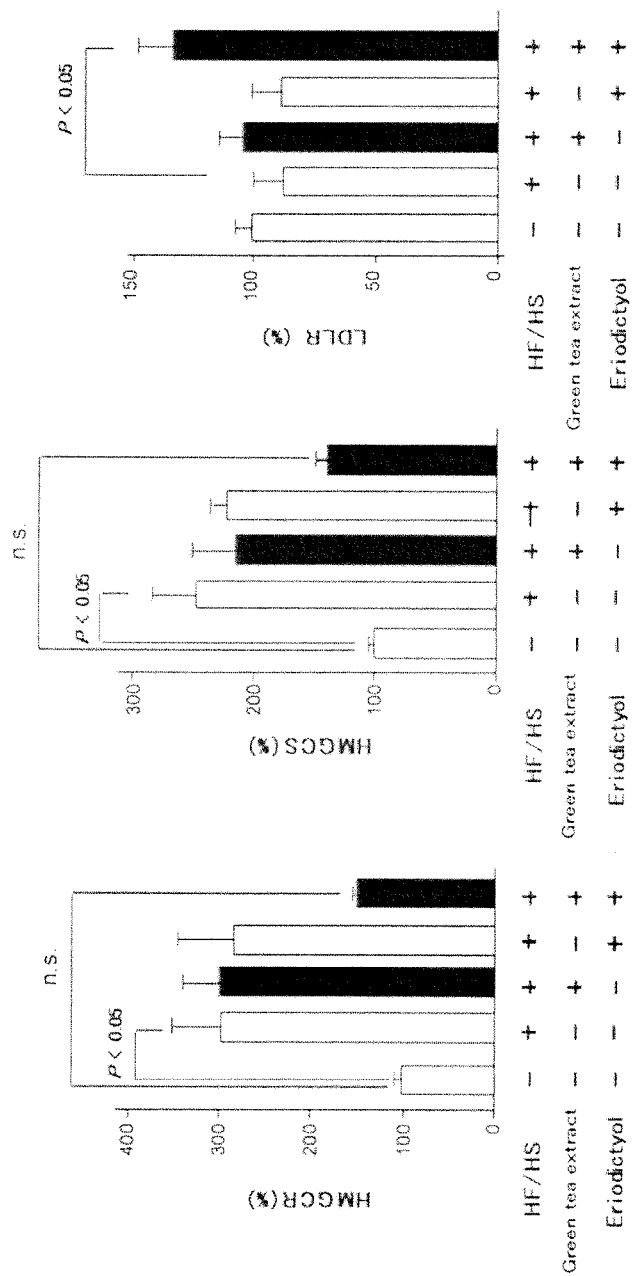
FIG. 6 shows the effect of combined intake of a green tea extract and eriodictyol on cholesterol metabolism-related gene expression in the liver of high-fat high-sucrose (HF/HS) diet-fed mice. C57BL/6J mice were fed with a diet supplemented with a green tea extract (0.2%) and eriodictyol (0.45 g/kg diet). After being kept for 8 weeks, the mice were measured for the mRNA expression levels of cholesterol metabolism-related genes in their liver by real-time PCR assay.

Effect of Combined Intake of a Green Tea Extract and Eriodictyol on Cholesterol Metabolism-Related Gene Expression in the Liver of High-Fat High-Sucrose (HF/HS) Diet-Fed Mice (FIG. 6)

Yabukita and eriodictyol were examined for their effect on cholesterol metabolism-related gene expression in the liver of high-fat high-sucrose diet-fed obese model mice. C57BL/6J mice were preliminarily kept for 1 week and then divided into the respective groups such that the average body weight was equal in all groups. Each feed was given in an amount of 4 g/day and the mice were kept for 8 weeks under ad libitum drinking conditions. After being fasted for 16 hours, the mice were sacrificed by abdominal aortic puncture under isoflurane anesthesia. Liver tissues were treated with TRIzol and cDNAs were synthesized, followed by real-time PCR to measure the mRNA expression levels of HMGCR, HMCGS and LDLR.

As a result, no effect was observed in the group receiving Yabukita or eriodictyol alone, whereas the group receiving Yabukita and eriodictyol in combination showed reduced expression levels of HMGCR and HMCGS in the liver and an increased expression level of LDLR in the liver.

Example 7

Figure 7:
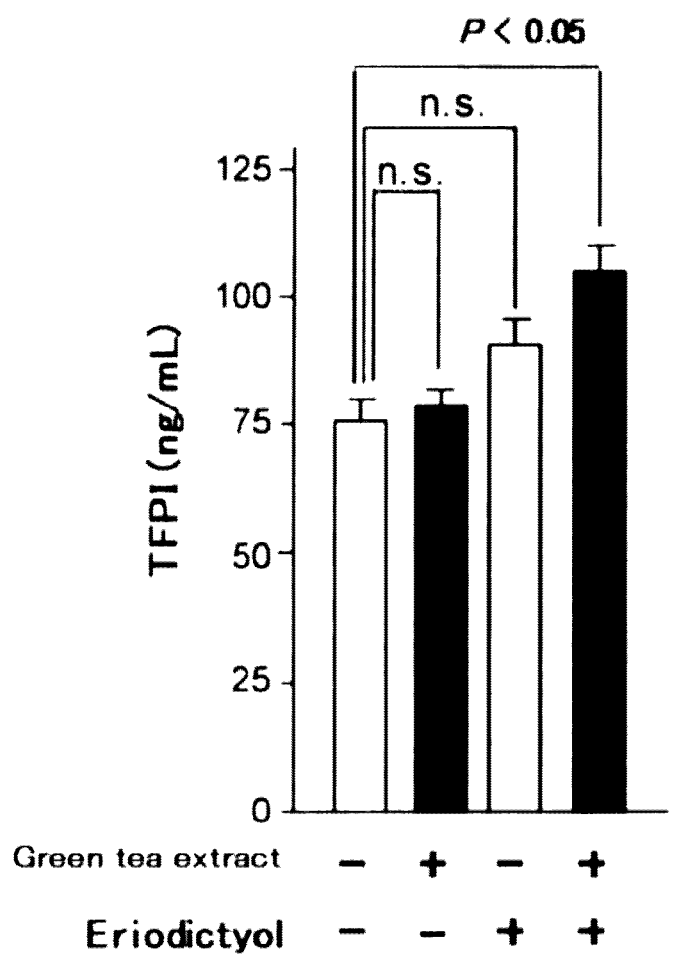
FIG. 7 shows the effect of combined intake of a green tea extract and eriodictyol on antithrombotic factor production. C57BL/6J mice were fed with a diet supplemented with a green tea extract (0.2%) and eriodictyol (0.45 g/kg diet). After being kept for 8 weeks, the mice were measured for the serum level of TFPI by ELISA assay.

Effect of Combined Intake of a Green Tea Extract and Eriodictyol on Antithrombotic Factor Production (FIG. 7)

Yabukita and eriodictyol were examined for their effect on antithrombotic factor production in mice. Male C57BL/6J mice at 12 weeks of age were preliminarily kept for 1 week and then divided into the respective groups such that the average body weight was equal in all groups. Each feed was given in an amount of 4 g/day and the mice were kept for 8 weeks under ad libitum drinking conditions. After being fasted for 16 hours, the mice were sacrificed by abdominal aortic puncture under isoflurane anesthesia. Blood samples collected by puncture were allowed to stand at 37° C. for 2 hours to cause coagulation and then centrifuged at 4° C. at 2000×g for 15 minutes to collect serum fractions. The serum level of TFPI, an antithrombotic factor, was measured by ELISA assay.

As a result, the group receiving Yabukita alone showed no effect, whereas the group receiving Yabukita and eriodictyol in combination showed an increased expression level of TFPI.

Example 8

Figure 8:
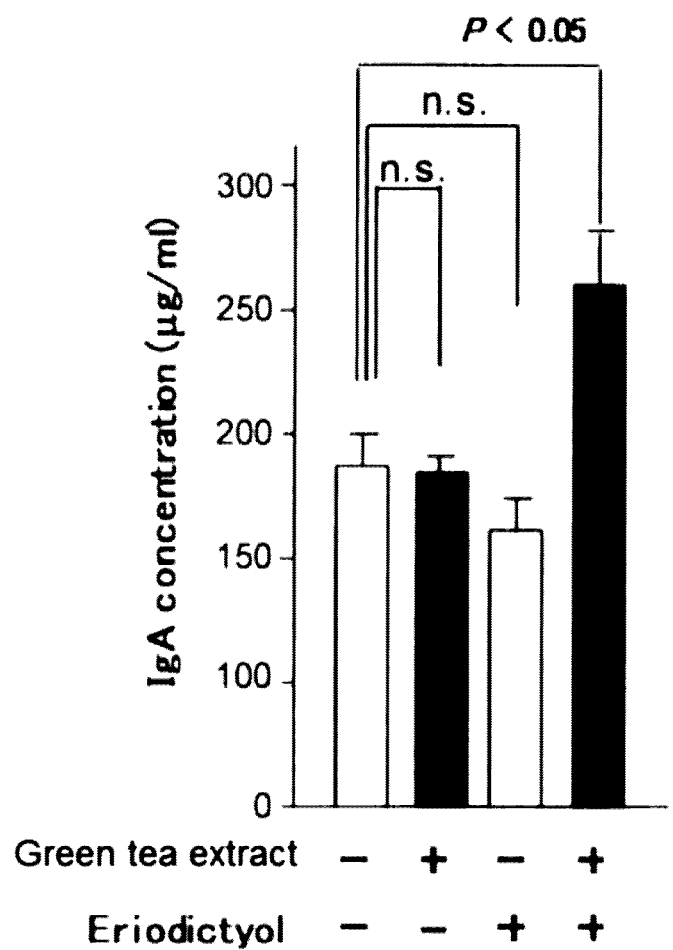
FIG. 8 shows the effect of combined intake of a green tea extract and eriodictyol on the serum level of IgA. C57BL/6J mice were fed with a diet supplemented with a green tea extract (0.2%) and eriodictyol (0.45 g/kg diet). After being kept for 8 weeks, the mice were measured for the serum level of IgA by ELISA assay.

Effect of Combined Intake of a Green Tea Extract and Eriodictyol on the Serum Level of IgA (FIG. 8)

Yabukita and eriodictyol were examined for their effect on the serum level of IgA in mice. Male C57BL/6J mice at 12 weeks of age were preliminarily kept for 1 week and then divided into the respective groups such that the average body weight was equal in all groups. Each feed was given in an amount of 4 g/day and the mice were kept for 8 weeks under ad libitum drinking conditions. After being fasted for 16 hours, the mice were sacrificed by abdominal aortic puncture under isoflurane anesthesia. Blood samples collected by puncture were allowed to stand at 37° C. for 2 hours to cause coagulation and then centrifuged at 4° C. at 2000×g for 15 minutes to collect serum fractions. The serum level of IgA was measured by ELISA assay.

As a result, the group receiving Yabukita alone showed no effect, whereas the group receiving Yabukita and eriodictyol in combination showed an increased level of IgA.

Example 9

Figure 9:
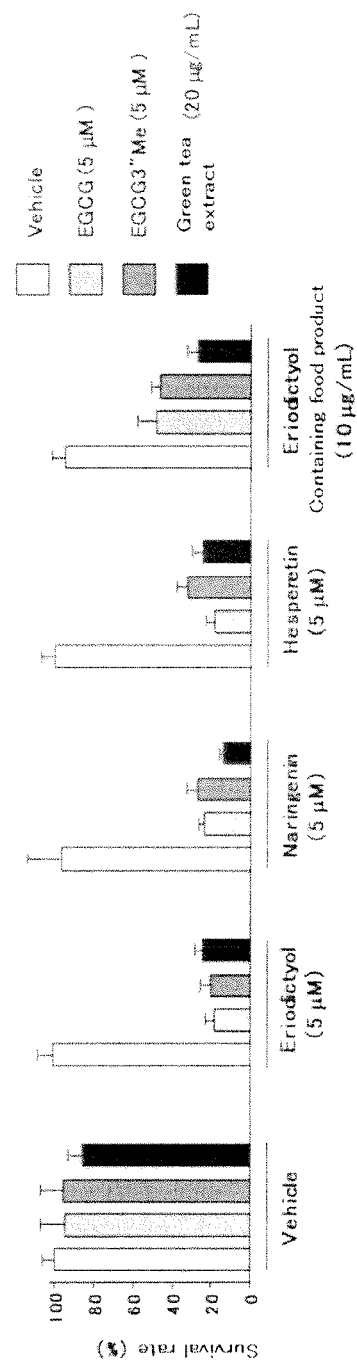
FIG. 9 shows the effect of combination with eriodictyol, an eriodictyol-related substance (naringenin, hesperetin) or an eriodictyol-containing food product extract on the cancer cell death induction activity of EGCG, EGCG 3"Me or a green tea extract. Human multiple myeloma cell line U266 was seeded in a 96-well plate ($5\times10^4$ cells/mL) and cultured for 96 hours in a medium supplemented with each ingredient. The cells were collected and viable cells were counted by trypan blue assay.

Effect of Combination with Eriodictyol, an Eriodictyol-Related Substance (Naringenin, Hesperetin) or an Eriodictyol-Containing Food Product Extract on the Cancer Cell Death Induction Activity of EGCG, EGCG 3"Me or a Green Tea Extract (FIG. 9)

To evaluate the effect of combined use of EGCG or a structural analog thereof or an EGCG-containing naturally occurring product and eriodictyol or a structural analog thereof or an eriodictyol-containing naturally occurring product, human multiple myeloma cell line U266 was adjusted to $5\times10^4$ cells/mL and seeded in a 96-well plate, and then cultured for 96 hours in the presence of EGCG and eriodictyol added at a final concentration of 5 μM each. After culture for 96 hours, viable cells were counted by trypan blue assay.

As a result, eriodictyol or a structural analog thereof, i.e., naringenin or hesperetin and an eriodictyol-containing lemon extract were found to remarkably enhance the anticancer effect of EGCG, EGCG "Me or a green tea extract.

Example 10

Figure 10:
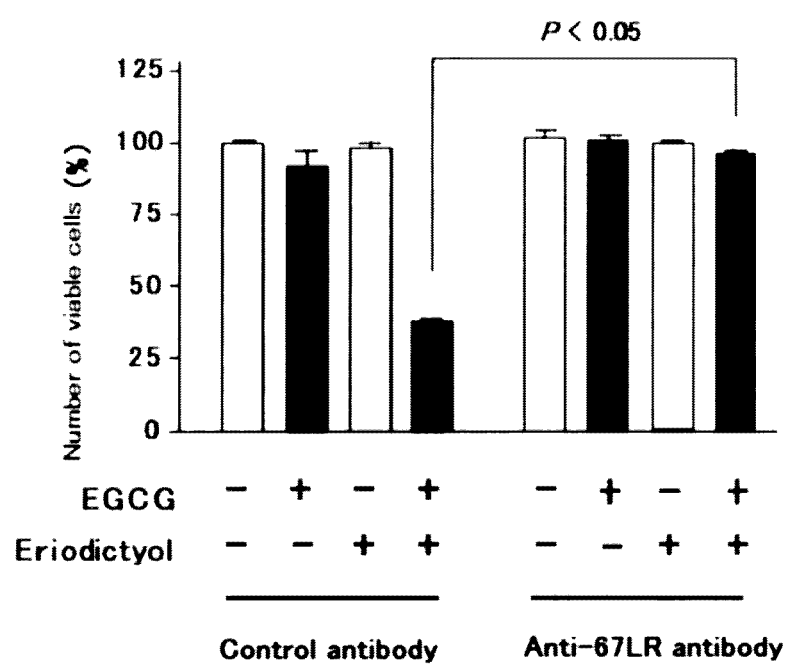
FIG. 10 shows the 67LR dependency of eriodictyol-induced EGCG activity enhancement. Human multiple myeloma cell line U266 was seeded in a 96-well plate ($5\times10^4$ cells/mL) and treated with anti-67LR antibody (20 µg/mL) for 3 hours. The cells were then cultured for 96 hours in a medium containing 5 µM eriodictyol and supplemented with EGCG at a final concentration of 5 µM, and viable cells were counted.

67LR Dependency of Eriodictyol-Induced EGCG Activity Enhancement (FIG. 10)

To examine the 67LR dependency of eriodictyol-induced EGCG activity enhancement, U266 cells were adjusted to $5\times10^4$ cells/mL and seeded in a 96-well plate, followed by addition of anti-67LR antibody at a final concentration of 20 μg/mL. After 3 hours, eriodictyol and EGCG were added to the medium at a final concentration of 5 μM each. After culture for 96 hours, viable cells were counted by ATPlite One Step (Perkin Elmer).

As a result, the anticancer effect upon combined use of EGCG and eriodictyol disappeared by pretreatment with anti-67LR antibody. This indicated that the enhancement effect of eriodictyol on the physiological activity of EGCG was dependent on 67LR.

Example 11

Figure 11:
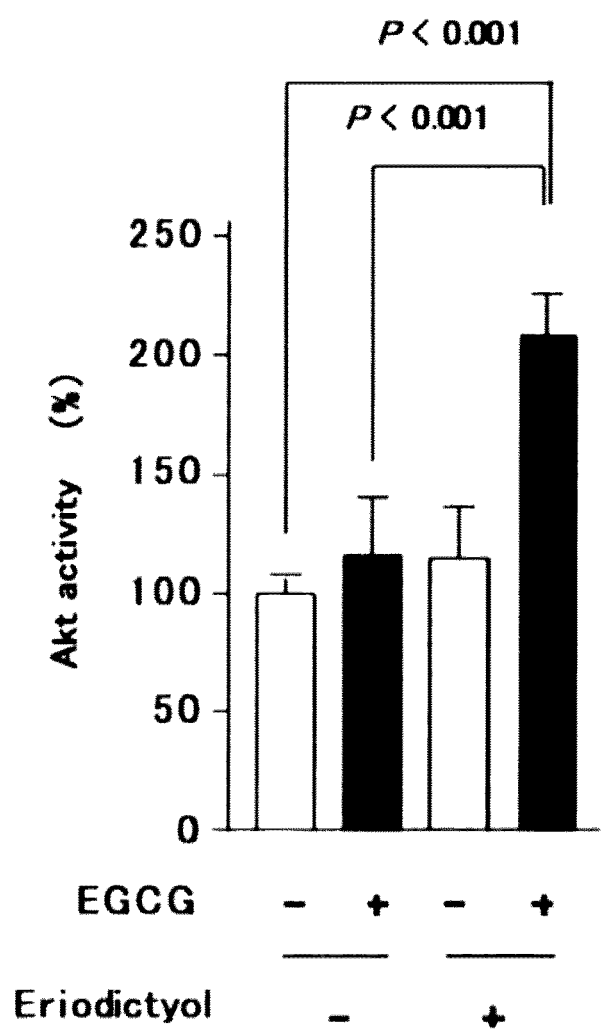
FIG. 11 shows the enhancement effect of eriodictyol on the ability of EGCG to induce Akt activation. Multiple myeloma cell line MPC-11 was implanted ($1\times10^6$ cells) by subcutaneous injection into the right dorsal region of Balb/c mice, followed by administration of EGCG (15 mg/kg) and eriodictyol (15 mg/kg). After 6 hours, tumors were excised and collected with a lysis buffer, followed by measurement of Akt activity.

Enhancement Effect of Eriodictyol on the Ability of EGCG to Induce Akt Activation (FIG. 11)

To examine the effect of eriodictyol on EGCG-induced activation of Akt responsible for 67LR-dependent cancer cell death induction activity, Balb/c mice were implanted with mouse multiple myeloma cell line MPC-11 by subcutaneous injection. At 11 days after implantation, the mice were administered with EGCG (15 mg/kg i.p.) and eriodictyol (15 mg/kg i.p.) and then sacrificed after 6 hours, followed by measurement of Akt activity in the excised tumors.

As a result, the combine use of eriodictyol and EGCG was found to remarkably increase Akt activity. This indicated that eriodictyol enhanced the EGCG-induced activation of 67LR signaling under in vivo conditions.

Example 12

Figure 12:
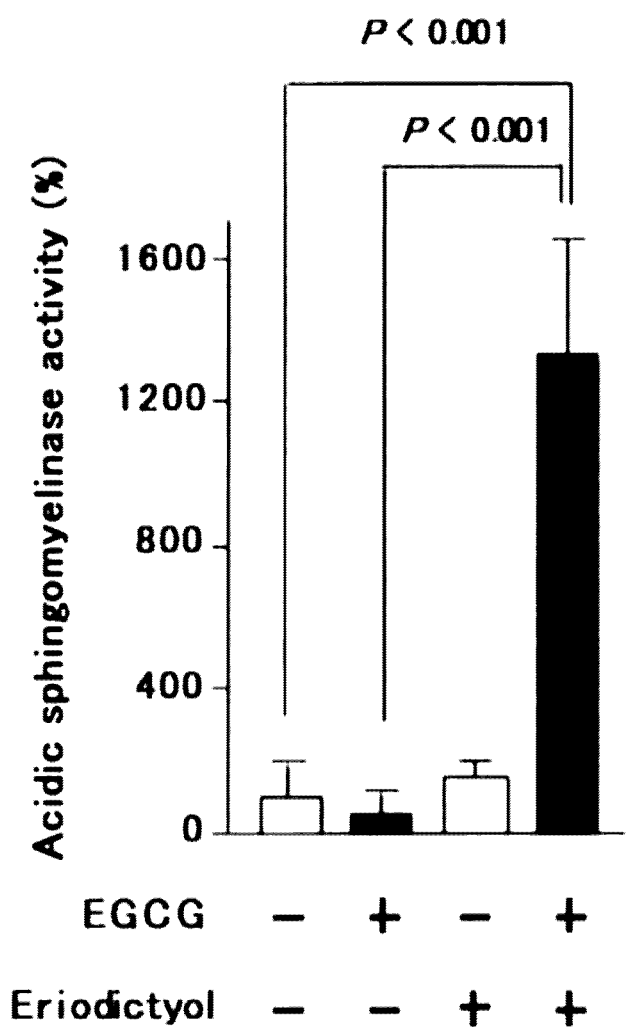
FIG. 12 shows the enhancement effect of eriodictyol on EGCG-induced activation of the 67LR-dependent cancer cell death induction pathway (acid sphingomyelinase activation). Multiple myeloma cell line MPC-11 was implanted ($1\times10^6$ cells) by subcutaneous injection into the right dorsal region of Balb/c mice, followed by administration of EGCG (15 mg/kg) and eriodictyol (15 mg/kg). After 6 hours, tumors were excised and collected with a lysis buffer, followed by measurement of acid sphingomyelinase activity.

Enhancement Effect of Eriodictyol on EGCG-Induced Activation of the 67LR-Dependent Cancer Cell Death Induction Pathway (Acid Sphingomyelinase Activation) (FIG. 12)

To examine the effect of eriodictyol on EGCG-induced activation of acid sphingomyelinase responsible for 67LR-dependent cancer cell death induction activity, Balb/c mice were implanted with mouse multiple myeloma cell line MPC-11 by subcutaneous injection. At 11 days after implantation, the mice were administered with EGCG (15 mg/kg i.p.) and eriodictyol (15 mg/kg i.p.) and then sacrificed after 6 hours, followed by measurement of acid sphingomyelinase activity in the excised tumors.

As a result, the combined use of eriodictyol and EGCG was found to remarkably increase acid sphingomyelinase activity. This indicated that eriodictyol enhanced the EGCG-induced activation of 67LR signaling under in vivo conditions.

Example 13

Figure 13:
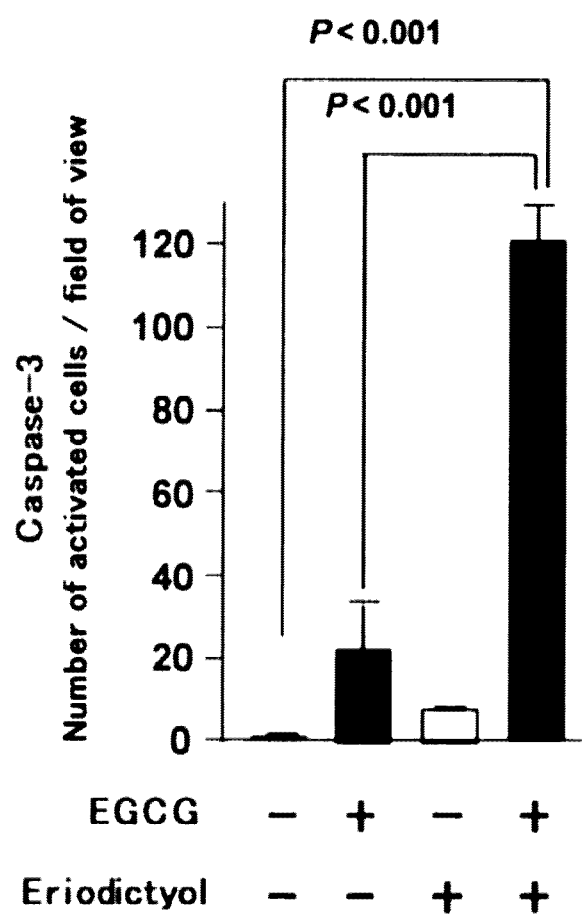
FIG. 13 shows the enhancement effect of eriodictyol on EGCG-induced 67LR-dependent cancer cell death activity (caspase-3 activity). Multiple myeloma cell line MPC-11 was implanted ($1\times10^6$ cells) by subcutaneous injection into the right dorsal region of Balb/c mice, followed by administration of EGCG (15 mg/kg) and eriodictyol (15 mg/kg). After 6 hours, tumors were excised. Tissue sections were prepared from the tumors and stained by immunohistological staining to determine the ratio of cells where caspase-3 was activated.

Enhancement Effect of Eriodictyol on EGCG-Induced 67LR-Dependent Cancer Cell Death Activity (Caspase-3 Activity) (FIG. 13)

To examine the effect of eriodictyol on EGCG-induced activation of caspase-3 indicative of 67LR-dependent cancer cell death induction mechanism activity, female balb/c mice at 5 weeks of age were implanted with mouse multiple myeloma cell line MPC-11 by subcutaneous injection. At 11 days after implantation, the mice were administered with EGCG (15 mg/kg i.p.) and eriodictyol (15 mg/kg i.p.) and then sacrificed after 6 hours. Tissue sections were prepared from the excised tumors and evaluated for the activation state of caspase-3.

As a result, eriodictyol was found to remarkably enhance the ability of EGCG to induce caspase-3 activation.

Experimental Procedures (2)
Effect of Combination with Eriodictyol or an Analog Thereof on the Anticancer Effect of EGCG or an Analog Thereof Human multiple myeloma cell line U266 was subcultured and maintained in RPMI 1640 medium supplemented with 10% fetal bovine serum (FCS) under conditions of 37° C. and water vapor-saturated 5% $CO_2$. The cells were maintained in the logarithmic growth phase. The RPMI 1640 medium used for culture was prepared as follows: per liter of ultrapure water, RPMI 1640 medium (10.4 g), HEPES (2.38 g), injectable penicillin G potassium (100,000 units), streptomycin sulfate injectable (100 mg) and $NaHCO_3$ (2.0 g) were suspended and then filter-sterilized. Then, the RPMI 1640 medium was supplemented with FCS and used for cell culture. Per liter of ultrapure water, NaCl (8.0 g), KCl (0.2 g), $Na_2HPO_4$ (1.15 g) and $KH_2PO_4$ (0.2 g) were dissolved to prepare PBS, which was then sterilized in an autoclave.

Eriodictyol and structural analogs thereof, i.e., naringenin and hesperetin, as well as glycosides thereof, i.e., eriocitrin, naringin and hesperidin were each adjusted to 5 mM with 100% dimethyl sulfoxide (DMSO) and stored at –30° C. EGCG and (–)-gallocatechin gallate (GCG) were each adjusted to 5 mM with ultrapure water and stored at –30° C. EGCG 3"Me was adjusted to 5 mM with 10% DMSO $dH_2O$ and stored at –30° C.

U266 adjusted to $5 \times 10^4$ cells/mL in RPMI 1640 containing 1% FCS, SOD (5 U/mL) and catalase (200 U/mL) was seeded in 24-well plates and cultured for 96 hours in the presence of EGCG and analogs thereof or eriodictyol and analogs thereof added at a final concentration of 5 µM each. After culture, viable cells were counted by trypan blue assay.

Statistics

For statistical processing of the experimental results, Student's test was used and P<0.05 was considered statistically significant in comparison with control data in the vehicle group.

Example 14

Influence of Eriodictyol on the Anticancer Effect of EGCG and Structural Analogs Thereof To evaluate the effect of eriodictyol on the anticancer effect of EGCG and structural analogs thereof, human multiple myeloma cell line U266 was adjusted to $5 \times 10^4$ cells/mL and seeded in 24-well plates, and then cultured for 96 hours in the presence of eriodictyol and structural analogs thereof added at a final concentration of 5 µM each. After culture for 96 hours, viable cells were counted by trypan blue assay.

Figure 14:
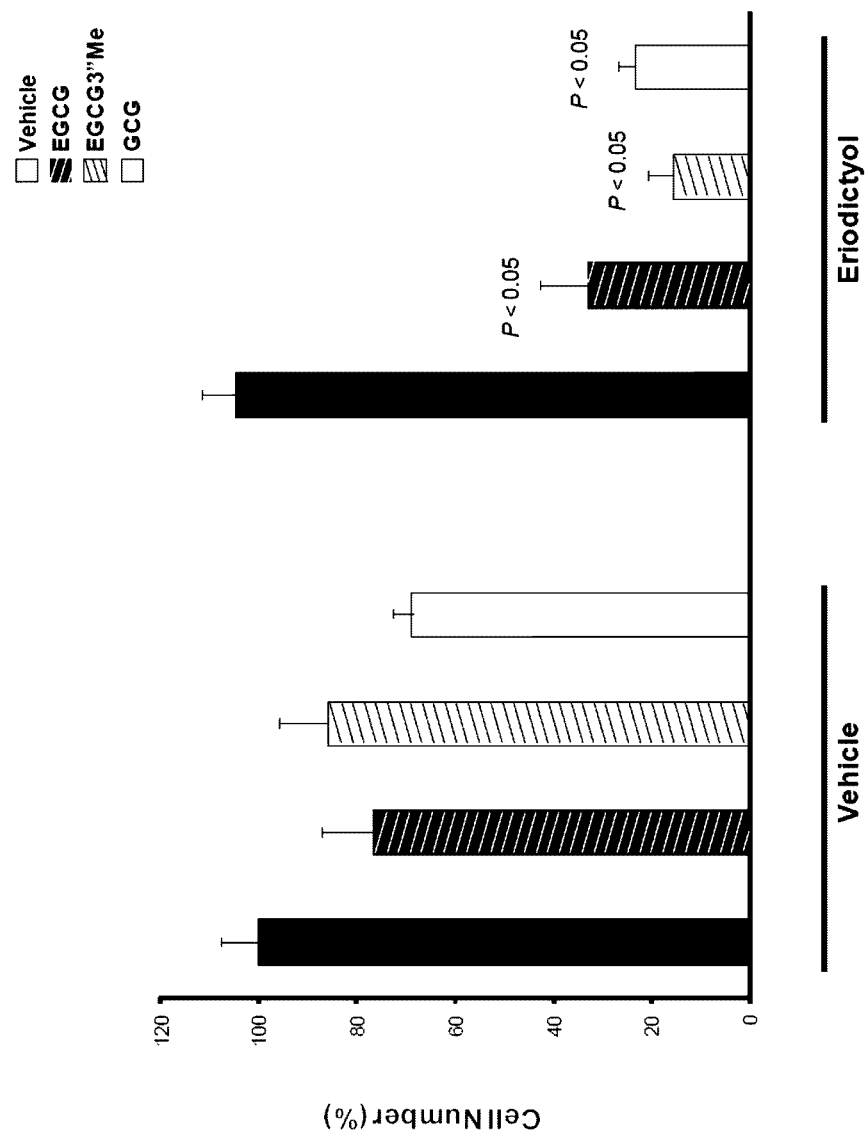
FIG. 14 shows the influence of eriodictyol on the anticancer effect of EGCG and structural analogs thereof. Human multiple myeloma cell line U266 was seeded in 24-well plates at $5\times10^4$ cells/mL in RPMI 1640 medium containing SOD (5 U/mL), catalase (200 U/mL) and 1% FCS, followed by addition of each ingredient. After 96 hours, viable cells were counted by trypan blue assay.

As a result, eriodictyol was found to remarkably enhance the anticancer effect of EGCG and structural analogs thereof, i.e., EGCG 3"Me and GCG (gallocatechin gallate) (FIG. 14).

Example 15

Influence of Naringenin on the Anticancer Effect of EGCG and Structural Analogs Thereof To evaluate the effect of naringenin on the anticancer effect of EGCG and structural analogs thereof, human multiple myeloma cell line U266 was adjusted to $5 \times 10^4$ cells/mL and seeded in 24-well plates, and then cultured for 96 hours in the presence of naringenin and structural analogs thereof added at a final concentration of 5 each. After culture for 96 hours, viable cells were counted by trypan blue assay.

Figure 15:
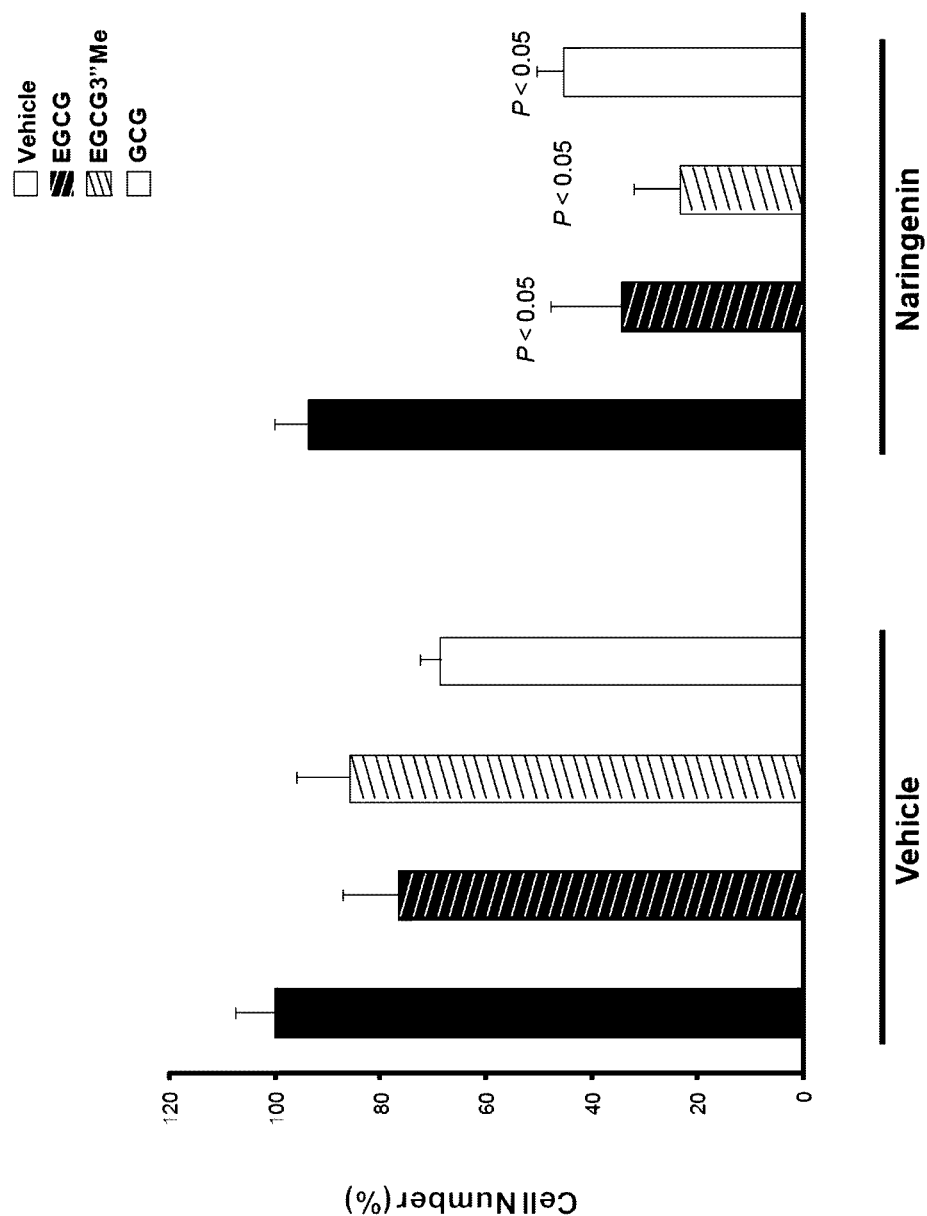
FIG. 15 shows the influence of naringenin on the anticancer effect of EGCG and structural analogs thereof. Human multiple myeloma cell line U266 was seeded in 24-well plates at $5\times10^4$ cells/mL in RPMI 1640 medium containing SOD (5 U/mL), catalase (200 U/mL) and 1% FCS, followed by addition of each ingredient. After 96 hours, viable cells were counted by trypan blue assay.

As a result, naringenin was found to remarkably enhance the anticancer effect of EGCG and structural analogs thereof, i.e., EGCG 3"Me and GCG (FIG. 15).

Example 16

Influence of Hesperetin on the Anticancer Effect of EGCG and Structural Analogs Thereof To evaluate the effect of hesperetin on the anticancer effect of EGCG and structural analogs thereof, human multiple myeloma cell line U266 was adjusted to $5 \times 10^4$ cells/mL and seeded in 24-well plates, and then cultured for 96 hours in the presence of hesperetin and structural analogs thereof added at a final concentration of 5 µM each. After culture for 96 hours, viable cells were counted by trypan blue assay.

Figure 16:
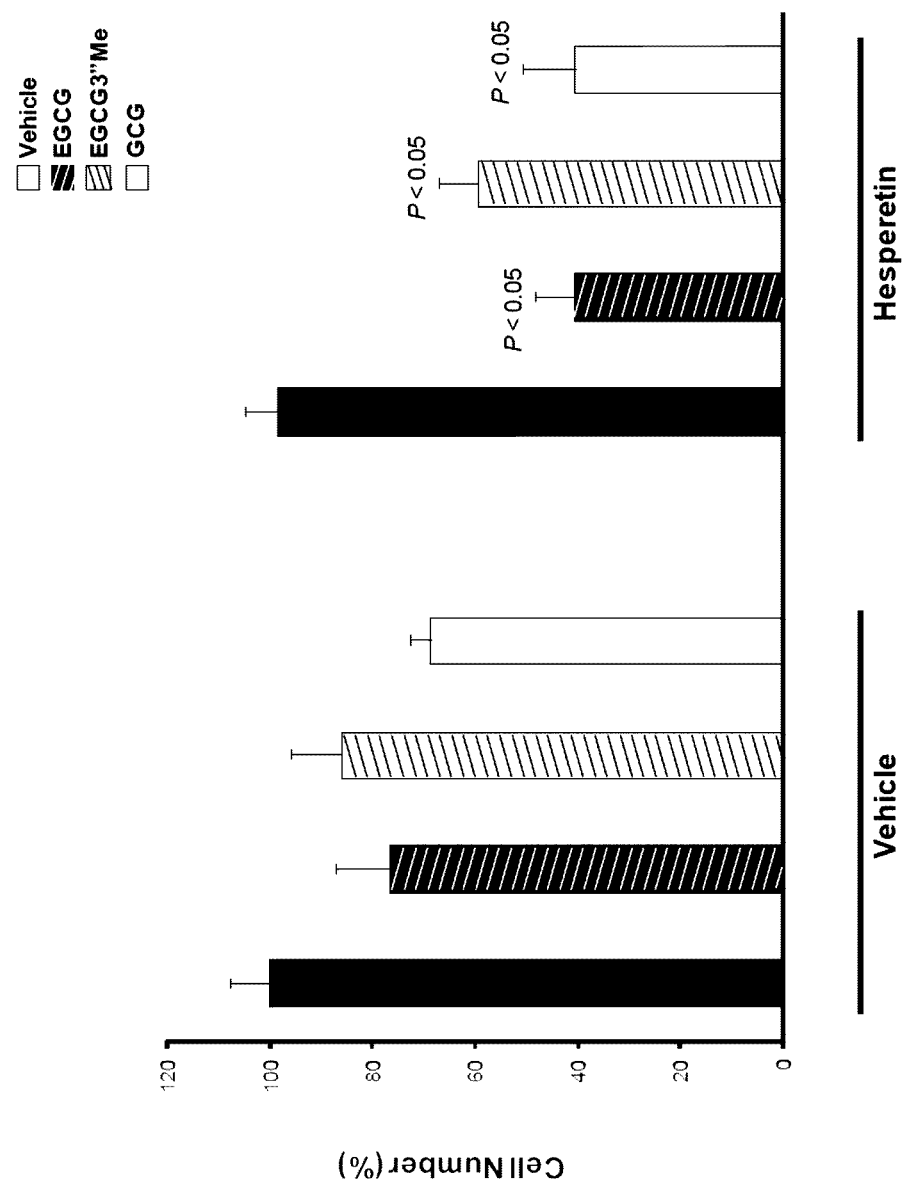
FIG. 16 shows the influence of hesperetin on the anticancer effect of EGCG and structural analogs thereof. Human multiple myeloma cell line U266 was seeded in 24-well plates at $5\times10^4$ cells/mL in RPMI 1640 medium containing SOD (5 U/mL), catalase (200 U/mL) and 1% FCS, followed by addition of each ingredient. After 96 hours, viable cells were counted by trypan blue assay.

As a result, hesperetin was found to remarkably enhance the anticancer effect of EGCG and structural analogs thereof, i.e., EGCG 3"Me and GCG (FIG. 16).

Example 17

Influence of Eriocitrin, an Eriodictyol Glycoside, on the Anticancer Effect of EGCG and Structural Analogs Thereof To evaluate the effect of eriocitrin on the anticancer effect of EGCG and structural analogs thereof, human multiple myeloma cell line U266 was adjusted to $5 \times 10^4$ cells/mL and seeded in 24-well plates, and then cultured for 96 hours in the presence of eriocitrin and structural analogs thereof added at a final concentration of 5 each. After culture for 96 hours, viable cells were counted by trypan blue assay.

Figure 17:
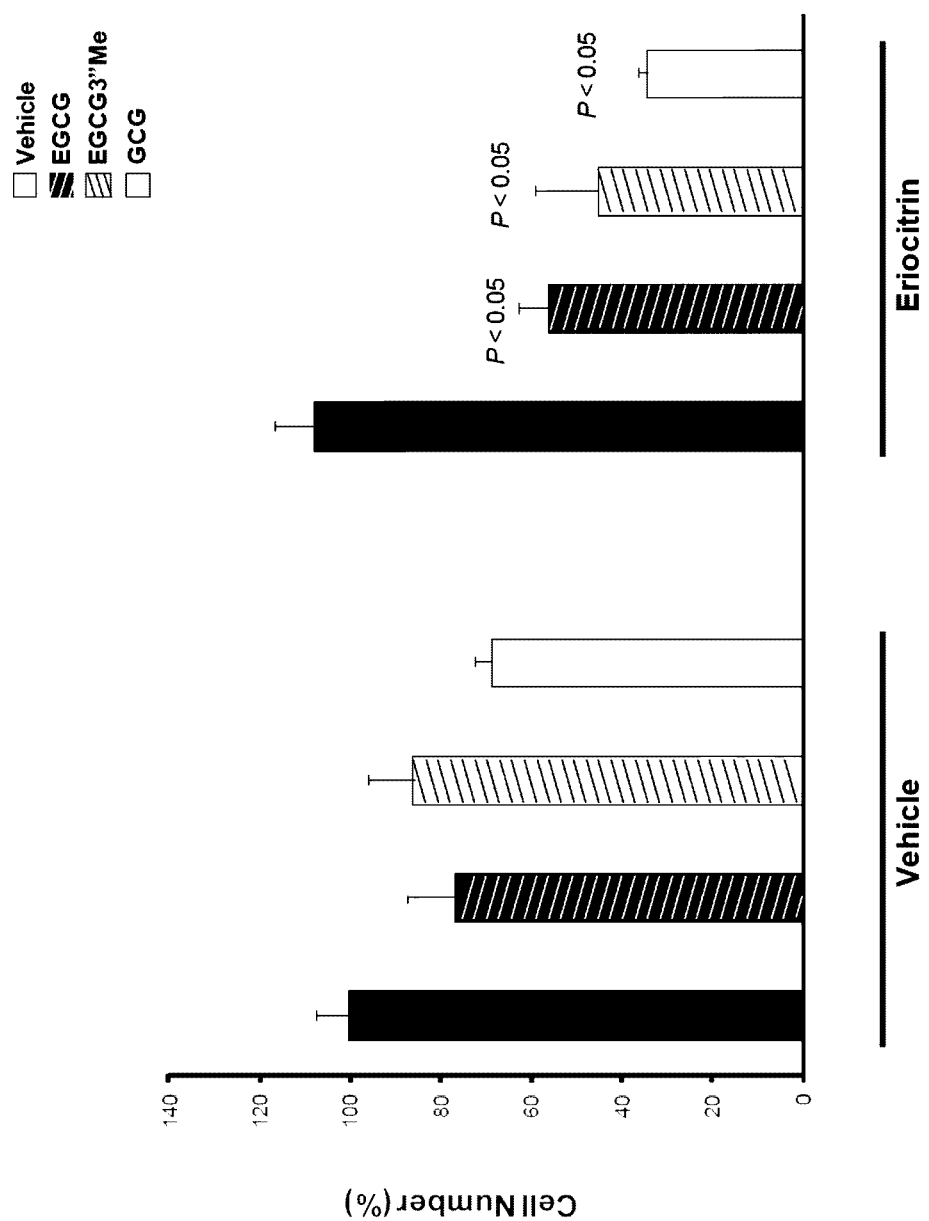
FIG. 17 shows the influence of eriocitrin on the anticancer effect of EGCG and structural analogs thereof. Human multiple myeloma cell line U266 was seeded in 24-well plates at $5\times10^4$ cells/mL in RPMI 1640 medium containing SOD (5 U/mL), catalase (200 U/mL) and 1% FCS, followed by addition of each ingredient. After 96 hours, viable cells were counted by trypan blue assay.

As a result, eriocitrin was found to remarkably enhance the anticancer effect of EGCG and structural analogs thereof, i.e., EGCG 3"Me and GCG (FIG. 17).

Example 18

Influence of Naringin, a Naringenin Glycoside, on the Anticancer Effect of EGCG and Structural Analogs Thereof To evaluate the effect of naringin on the anticancer effect of EGCG and structural analogs thereof, human multiple myeloma cell line U266 was adjusted to $5\times10^4$ cells/mL and seeded in 24-well plates, and then cultured for 96 hours in the presence of naringin and structural analogs thereof added at a final concentration of 5 μM each. After culture for 96 hours, viable cells were counted by trypan blue assay.

Figure 18:
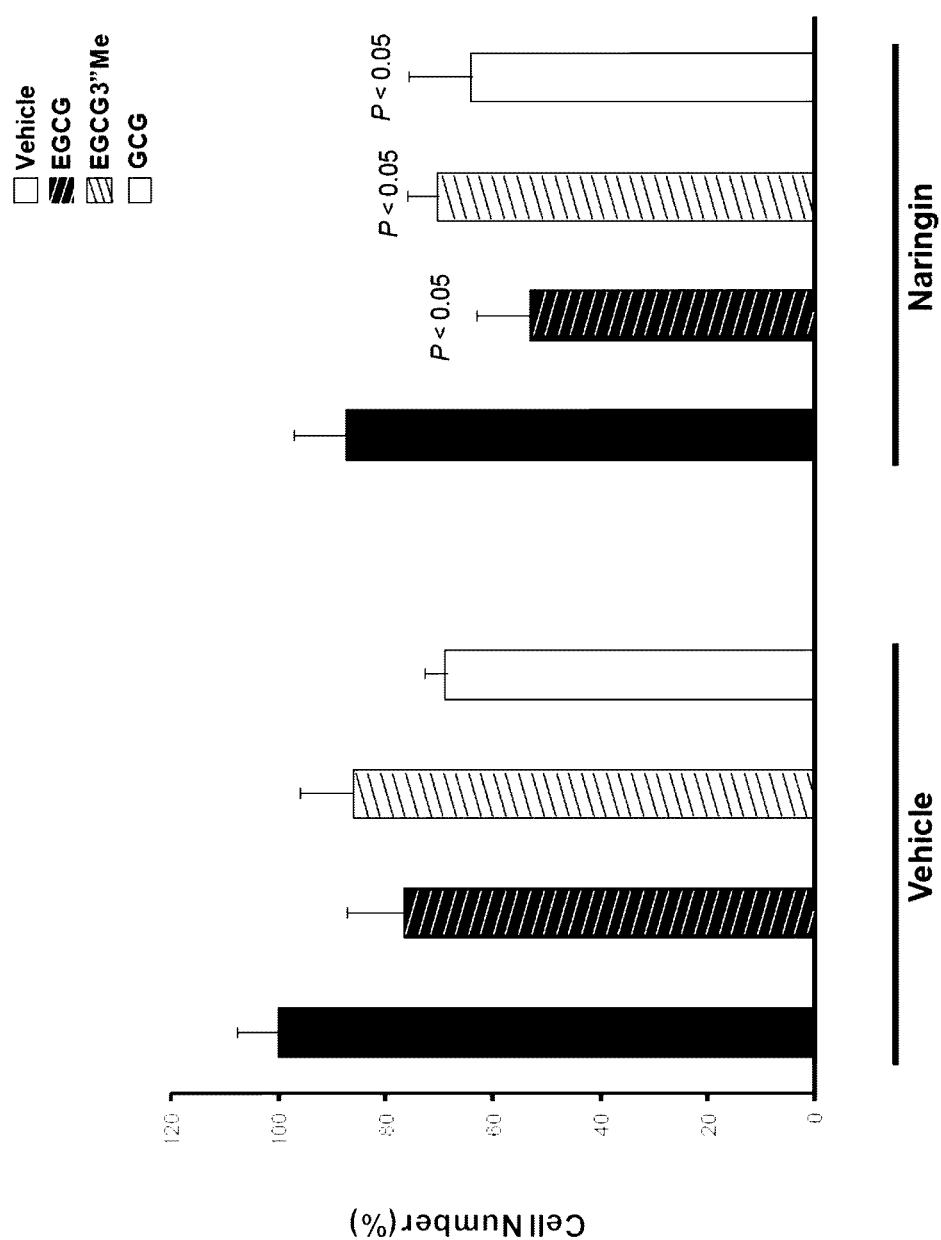
FIG. 18 shows the influence of naringin on the anticancer effect of EGCG and structural analogs thereof. Human multiple myeloma cell line U266 was seeded in 24-well plates at $5\times10^4$ cells/mL in RPMI 1640 medium containing SOD (5 U/mL), catalase (200 U/mL) and 1% FCS, followed by addition of each ingredient. After 96 hours, viable cells were counted by trypan blue assay.

As a result, naringin was found to remarkably enhance the anticancer effect of EGCG (FIG. 18).

Example 19

Influence of Hesperidin, a Hesperetin Glycoside, on the Anticancer Effect of EGCG and Structural Analogs Thereof To evaluate the effect of hesperidin on the anticancer effect of EGCG and structural analogs thereof, human multiple myeloma cell line U266 was adjusted to $5\times10^4$ cells/mL and seeded in 24-well plates, and then cultured for 96 hours in the presence of hesperidin and structural analogs thereof added at a final concentration of 5 μM each. After culture for 96 hours, viable cells were counted by trypan blue assay.

Figure 19:
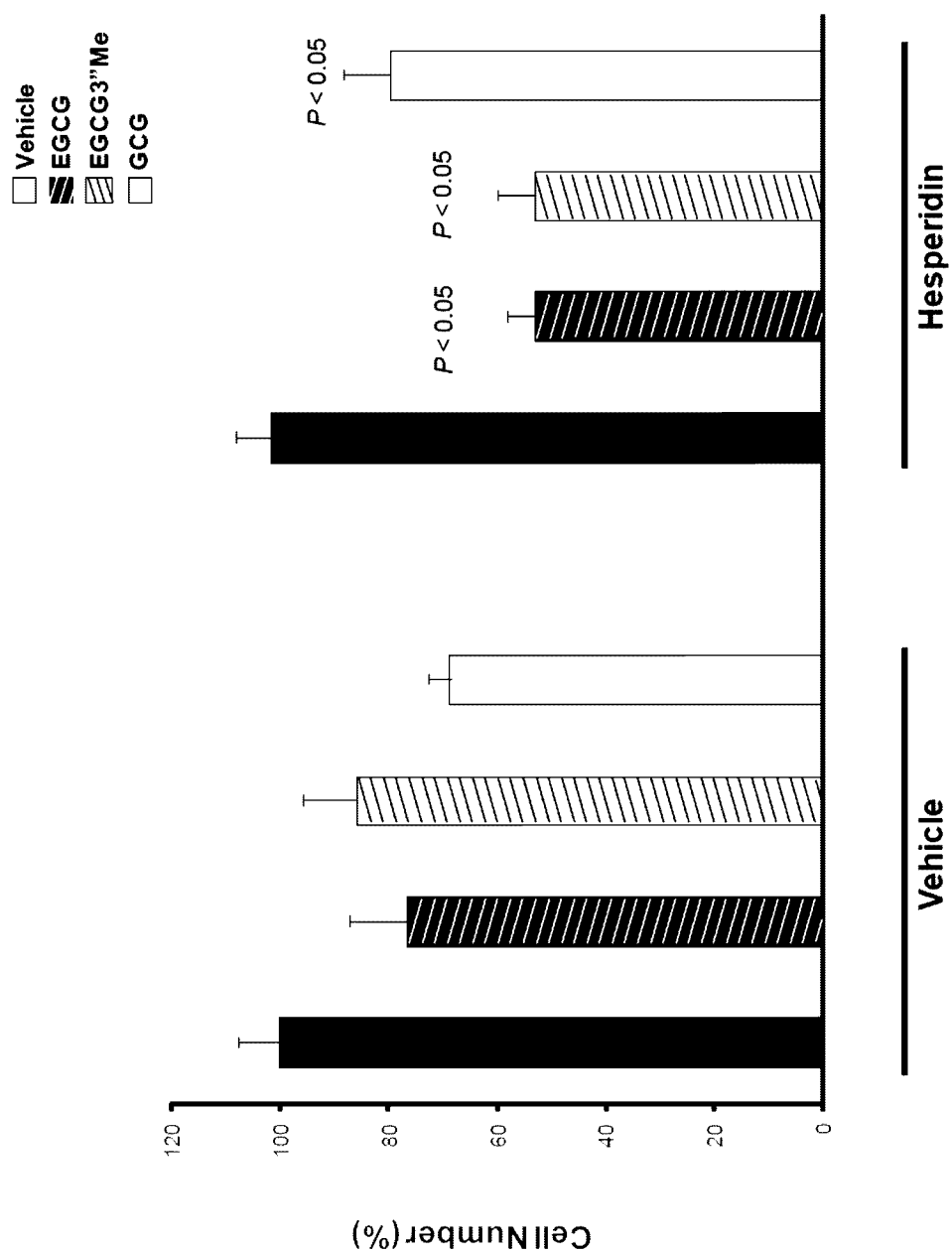
FIG. 19 shows the influence of hesperidin on the anticancer effect of EGCG and structural analogs thereof. Human multiple myeloma cell line U266 was seeded in 24-well plates at $5\times10^4$ cells/mL in RPMI 1640 medium containing SOD (5 U/mL), catalase (200 U/mL) and 1% FCS, followed by addition of each ingredient. After 96 hours, viable cells were counted by trypan blue assay.

As a result, hesperidin was found to remarkably enhance the anticancer effect of EGCG and structural analogs thereof, i.e., EGCG 3"Me and GCG (FIG. 19).

INDUSTRIAL APPLICABILITY

The composition of the present invention is useful as a functional food product having an anticancer effect, anti-inflammatory effect and other effects.

The invention claimed is:

1. A composition comprising:
a green tea extract or a catechin; and
a citrus fruit extract or a flavanone or a glycoside thereof,
wherein the green tea extract or catechin is at least one selected from the group consisting of epicatechin, epigallocatechin, epicatechin gallate, gallocatechin gallate, epigallocatechin gallate and methylated catechin, and the citrus fruit extract or flavanone or glycoside thereof is at least one selected from the group consisting of eriodictyol, hesperetin, eriodictyol glycoside, hesperetin glycoside and combinations thereof,
wherein a content of the green tea extract or catechin is 30% by weight to 0.001% by weight and a content of the citrus fruit extract or flavanone or glycoside thereof is 20% by weight to 0.001% by weight.

2. The composition according to claim 1, which has at least one effect selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect.

3. A functional food product comprising:
a green tea extract or a catechin; and
a citrus fruit extract or a flavanone or a flavanone glycoside,
wherein the green tea extract or catechin is at least one selected from the group consisting of epicatechin, epigallocatechin, epicatechin gallate, gallocatechin gallate, epigallocatechin gallate and methylated catechin, and the citrus fruit extract or flavanone or glycoside thereof is at least one selected from the group consisting of eriodictyol, hesperetin, eriodictyol glycoside, hesperetin glycoside and combinations thereof,
wherein a content of the green tea extract or catechin is 30% by weight to 0.001% by weight and a content of the citrus fruit extract or flavanone or glycoside thereof is 20% by weight to 0.001% by weight.

4. The food product according to claim 3, which has at least one effect selected from the group consisting of an anticancer effect, an anti-amyotrophic effect, an anti-obesity effect, an anti-inflammatory effect and a cholesterol-lowering effect, a prophylactic effect on thrombosis or cerebral infarction, and an immunostimulatory effect.

5. An agent comprising:
a green tea extract or a catechin; and
a citrus fruit extract or a flavanone or a glycoside thereof,
wherein the agent is selected from the group consisting of an anticancer agent, an anti-amyotrophic agent, an anti-obesity agent, an anti-inflammatory agent, a cholesterol-lowering agent, a prophylactic agent for thrombosis or cerebral infarction, and an immunostimulatory agent,
wherein the green tea extract or catechin is at least one selected from the group consisting of epicatechin, epigallocatechin, epicatechin gallate, gallocatechin gallate, epigallocatechin gallate and methylated catechin, and the citrus fruit extract or flavanone or glycoside thereof is at least one selected from the group consisting of eriodictyol, hesperetin, eriodictyol glycoside, hesperetin glycoside and combinations thereof,
wherein a content of the green tea extract or catechin is 30% by weight to 0.001% by weight and a content of the citrus fruit extract or flavanone or glycoside thereof is 20% by weight to 0.001% by weight.

6. An enhancer comprising:
a citrus fruit extract or a flavanone or a glycoside thereof for enhancement of at least one effect of a green tea extract or a catechin,
wherein the enhancer has at least one effect selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect,
wherein the green tea extract or catechin is at least one selected from the group consisting of epicatechin, epigallocatechin, epicatechin gallate, gallocatechin gallate, epigallocatechin gallate or methylated catechin, and the citrus fruit extract or flavanone or glycoside thereof is at least one selected from the group consisting of eriodictyol, hesperetin, eriodictyol glycoside, hesperetin glycoside and combinations thereof,
wherein a content of the green tea extract or catechin is 30% by weight to 0.001% by weight and a content of the citrus fruit extract or flavanone or glycoside thereof is 20% by weight to 0.001% by weight.

7. A method comprising feeding a subject in need thereof with the composition according to claim 1, to enhance at least one effect of the green tea extract or catechin in the subject, wherein the at least one effect is selected from the group consisting of an anticancer effect, an anti-amyotrophic effect, an anti-obesity effect, an anti-inflammatory effect, a cholesterol-lowering effect, a prophylactic effect on thrombosis or cerebral infarction, and an immunostimulatory effect.

* * * * *